(12) United States Patent
Staton et al.

(10) Patent No.: US 10,837,163 B2
(45) Date of Patent: *Nov. 17, 2020

(54) SMART URINALS AND METHODS OF MAKING AND USING SAME

(71) Applicant: NEWTONOID TECHNOLOGIES, L.L.C., Liberty, MO (US)

(72) Inventors: Fielding B. Staton, Liberty, MO (US); David Strumpf, Columbia, MO (US)

(73) Assignee: NEWTONOID TECHNOLOGIES, L.L.C., Liberty, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/431,449

(22) Filed: Feb. 13, 2017

(65) Prior Publication Data
US 2018/0163388 A1 Jun. 14, 2018

Related U.S. Application Data

(63) Continuation-in-part of application No. 15/378,005, filed on Dec. 13, 2016, now Pat. No. 10,604,924.

(51) Int. Cl.
*E03D 13/00* (2006.01)
*A61B 10/00* (2006.01)
(Continued)

(52) U.S. Cl.
CPC ........ *E03D 13/005* (2013.01); *A61B 5/14507* (2013.01); *A61B 5/20* (2013.01);
(Continued)

(58) Field of Classification Search
CPC . A61B 5/0002; A61B 10/007; A61B 5/14507;
A61B 5/7445; A61B 5/746; A61B 5/6891; A61B 5/207; A61B 5/20; G06Q 10/10; G06Q 50/22; G06F 19/3418; G06F 3/011; G06F 3/002; G06F 1/1601; E03D 13/005; E03D 13/00; A63F 13/245;
(Continued)

(56) References Cited

U.S. PATENT DOCUMENTS 3,745,592 A * 7/1973 Novak ..................... A61F 5/44
4/144.1
4,961,431 A 10/1990 Ikenaga et al.
(Continued)

OTHER PUBLICATIONS

U.S. Appl. No. 15/378,005, Non-Final Office Action dated Mar. 20, 2017, 17 pages.
(Continued)

*Primary Examiner* — Patrick Fernandes
(74) *Attorney, Agent, or Firm* — Avant Law Group, LLC

(57) ABSTRACT

A method for retrofitting a urinal having an interior part configured to receive urine voided by a user, and an exterior part. The method includes the step of providing a urinal retrofitting device. The urinal retrofitting device includes a processor, a memory, a projecting device, and a housing for housing the processor and the projecting device. The projecting device is located in the housing such that the projecting device projects user consumable content outside the housing at an angle. The housing is disposed adjacent the exterior part such that the user can consume the user consumable content while the user is urinating at the urinal.

20 Claims, 13 Drawing Sheets

(51) Int. Cl.
*A61B 5/145* (2006.01)
*A61B 5/00* (2006.01)
*A61B 5/20* (2006.01)
*G06F 3/01* (2006.01)
*G06F 3/00* (2006.01)
*G06F 1/16* (2006.01)
*A63F 13/245* (2014.01)
*G16H 40/63* (2018.01)
*A63F 13/30* (2014.01)
*A63F 13/837* (2014.01)
*A63F 13/25* (2014.01)
*A61B 5/117* (2016.01)
*A61B 5/1172* (2016.01)
*A61B 5/01* (2006.01)

(52) U.S. Cl.
CPC ............ *A61B 5/207* (2013.01); *A61B 5/6891* (2013.01); *A61B 5/746* (2013.01); *A61B 5/7445* (2013.01); *A61B 10/007* (2013.01); *A63F 13/245* (2014.09); *A63F 13/25* (2014.09); *A63F 13/30* (2014.09); *A63F 13/837* (2014.09); *E03D 13/00* (2013.01); *G06F 1/1601* (2013.01); *G06F 3/002* (2013.01); *G06F 3/011* (2013.01); *G16H 40/63* (2018.01); *A61B 5/0015* (2013.01); *A61B 5/0075* (2013.01); *A61B 5/01* (2013.01); *A61B 5/117* (2013.01); *A61B 5/1172* (2013.01); *A61B 2503/12* (2013.01); *A61B 2560/04* (2013.01); *A61B 2560/0462* (2013.01); *A61B 2562/06* (2013.01)

(58) Field of Classification Search
CPC ........ A63F 13/30; A63F 13/837; A63F 13/25; G16H 40/63
See application file for complete search history.

(56) References Cited

U.S. PATENT DOCUMENTS

| | | | |
|---|---|---|---|
| 5,882,931 A | | 3/1999 | Petersen et al. |
| 5,913,832 A | | 6/1999 | Sagalovich et al. |
| 5,926,867 A | * | 7/1999 | Buchanan .............. A47K 13/24 353/43 |
| 6,385,796 B1 | | 5/2002 | Muir, Jr. |
| 6,513,173 B1 | | 2/2003 | Sykes |
| 6,571,399 B1 | * | 6/2003 | Wagener ............... E03D 13/002 4/254 |
| 6,640,356 B1 | | 11/2003 | Hans |
| 2010/0005582 A1 | * | 1/2010 | Rao ........................ E03D 13/005 4/301 |
| 2010/0131334 A1 | * | 5/2010 | Firminger .............. G06Q 10/10 705/7.42 |
| 2010/0146691 A1 | | 6/2010 | Chan |
| 2010/0223139 A1 | * | 9/2010 | Bosan ................. G06Q 30/0267 705/14.64 |
| 2011/0050432 A1 | * | 3/2011 | MacSween ............. E03D 13/00 340/603 |
| 2011/0061274 A1 | | 3/2011 | Pascarelli et al. |
| 2012/0154169 A1 | * | 6/2012 | Hoekstra ................ G07F 17/18 340/870.01 |
| 2012/0227510 A1 | | 9/2012 | Grumbles, III et al. |
| 2013/0016197 A1 | * | 1/2013 | Koo ........................ E03D 13/00 348/61 |
| 2013/0019271 A1 | * | 1/2013 | Chiu ........................ E03D 5/10 725/80 |
| 2013/0216989 A1 | * | 8/2013 | Cuthbert ................ G09B 19/00 434/238 |
| 2013/0221618 A1 | | 8/2013 | Freriks |
| 2015/0000025 A1 | * | 1/2015 | clements ................. G06F 3/013 4/443 |
| 2015/0189356 A1 | * | 7/2015 | Shen ................... H04N 21/4126 725/34 |
| 2016/0000378 A1 | * | 1/2016 | Hall ..................... A61B 5/0075 702/19 |
| 2016/0097751 A1 | * | 4/2016 | Dron ..................... G01N 33/0001 73/23.34 |
| 2016/0171525 A1 | * | 6/2016 | Ezra ................... G06Q 30/0225 705/14.12 |
| 2016/0278705 A1 | * | 9/2016 | Han ..................... A61B 5/0002 |

OTHER PUBLICATIONS

U.S. Appl. No. 15/378,005, Final Office Action dated Jun. 13, 2017, 22 pages.
U.S. Appl. No. 15/378,005, Non-Final Office Action dated Jan. 30, 2018, 21 pages.
U.S. Appl. No. 15/378,005, Final Office Action dated Nov. 13, 2018.
U.S. Appl. No. 15/378,005, Non-Final Office Action dated Aug. 2, 2019, 14 pages.

* cited by examiner

| Name 304 | Device ID 306 | Health Screener Results 308 | Date;Time 310 | Name/City/ Geospatial Coordinates 312 | Rewards 314 | Biometric Sample 316 | Alert 318 | Recommendation 320 |
|---|---|---|---|---|---|---|---|---|
| John | 123456 | Drugs: No<br>Proteins: Normal<br>Color: Clear<br>. . .<br>Sugars: 300mg/dL<br>Bacteria: Normal | 11/1/2016 ;<br>2:00 pm | David's Bar/<br>Overland Park<br>KS/39.98° N,<br>94.67° W | Free Beer x2<br>at David's Bar | Finger Print | Your Blood Sugar is High | Visit a Doctor About Your Blood Sugar |

SMART URINALS AND METHODS OF MAKING AND USING SAME

CROSS-REFERENCE TO RELATED APPLICATIONS

This application is a continuation-in-part of U.S. patent application Ser. No. 15/378,005, filed Dec. 13, 2016, the disclosure of which is incorporated herein by reference in its entirety.

FIELD OF THE DISCLOSURE

The disclosure relates generally to the field of smart urinals. Specifically, the disclosure relates to interactive accessories for retrofitting urinals.

SUMMARY

The following presents a simplified summary of the invention in order to provide a basic understanding of some aspects of the invention. This summary is not an extensive overview of the invention. It is not intended to identify critical elements of the invention or to delineate the scope of the invention. Its sole purpose is to present some concepts of the invention in a simplified form as a prelude to the more detailed description that is presented elsewhere.

According to an embodiment, an accessory is configured for use with a urinal. The urinal has a body which includes an interior part and an exterior part. The interior part is configured to receive urine voided by a user. The accessory includes a processor, a sensor for sensing at least one characteristic of urine voided by the user on the interior part, and a networking device. The accessory also includes a projector that projects content for consumption by the user in response to a wireless communication between the networking device and a mobile device of the user. A housing accommodates the processor, the sensor, the networking device, and the projector. The housing is disposed atop the exterior part such that the projector projects the content for user consumption onto the interior part.

According to another embodiment, a method for retrofitting a urinal is provided. The urinal comprises an interior part and an exterior part. The interior part is configured to receive urine voided by a user. The method includes the step of providing a urinal retrofitting device. The urinal retrofitting device includes a processor, a memory, a projecting device, and a housing for housing the processor and the projecting device. The method includes the step of locating the projecting device in the housing such that the projecting device projects user consumable content outside the housing at an angle. The method also includes the step of disposing the housing adjacent the exterior part such that the user can consume the user consumable content while the user is urinating at the urinal.

According to yet another embodiment, an accessory configured for use with a urinal is disclosed. The urinal has a body which comprises an interior part and an exterior part. The interior part is configured to receive urine voided by a user. The accessory comprises a processor, a sensor sensing at least one characteristic of urine voided by the user on the interior part, and a networking device. The accessory includes a projector projecting content for consumption by the user. The accessory further includes a housing accommodating the processor, the sensor, the networking device, and the projector. The housing is configured to be disposed atop the exterior part to allow the projector to project the content for user consumption onto the interior part.

BRIEF DESCRIPTION OF THE SEVERAL VIEWS OF THE DRAWINGS

Illustrative embodiments of the present invention are described in detail below with reference to the attached drawing figures and wherein:

FIG. 7 shows an example user record created by the investigative computer of FIG. 5;

DETAILED DESCRIPTION

Commercial establishments such as bars, hotels, gyms, restaurants, etc., are constantly trying to find ways to increase patronage. For example, a gym may invest in a new exercising machine to lure new patrons. Or, for example, a bar may offer a signature drink to attract and retain customers. Such efforts may not always be successful, at least in part due to their limited appeal. A new exercising machine may not excite a potential patron who does not intend to use that particular machine. Similarly, a potential customer at a bar may not be partial to the ingredients of the particular signature drink being offered by the bar. One thing, however, may be common to all patrons—each of them, from time to time, will need to use a restroom to empty his or her respective bladder. For all male patrons, this may translate to a trip to a urinal at the commercial establishment. A urinal configured to allow users to functionally interact with the urinal may thus be of immediate interest to a large segment of commercial entities' patrons.

Patrons of establishments may also be interested in monitoring their health. Numerous recent studies show that consumers, on average, are more conscious about their health than ever before. Traditionally, to monitor one's health, an individual may visit a physician, who may procure a sample of the individual's blood, skin, urine, etc., and send same to a lab for testing and analysis. This process may be costly and time consuming, which may deter individuals from quantitatively and/or qualitatively monitoring their health on a regular basis. Equipping a urinal—which male members of the society may use several times a day in any event—with health monitoring capabilities may be an easy and convenient way to allow men (and other users of urinals) to monitor their health on regular basis. The present disclosure relates at least in part to a smart urinal which may have associated therewith a novelty factor and/or which may be used by individuals to monitor their health.

Figure 1:
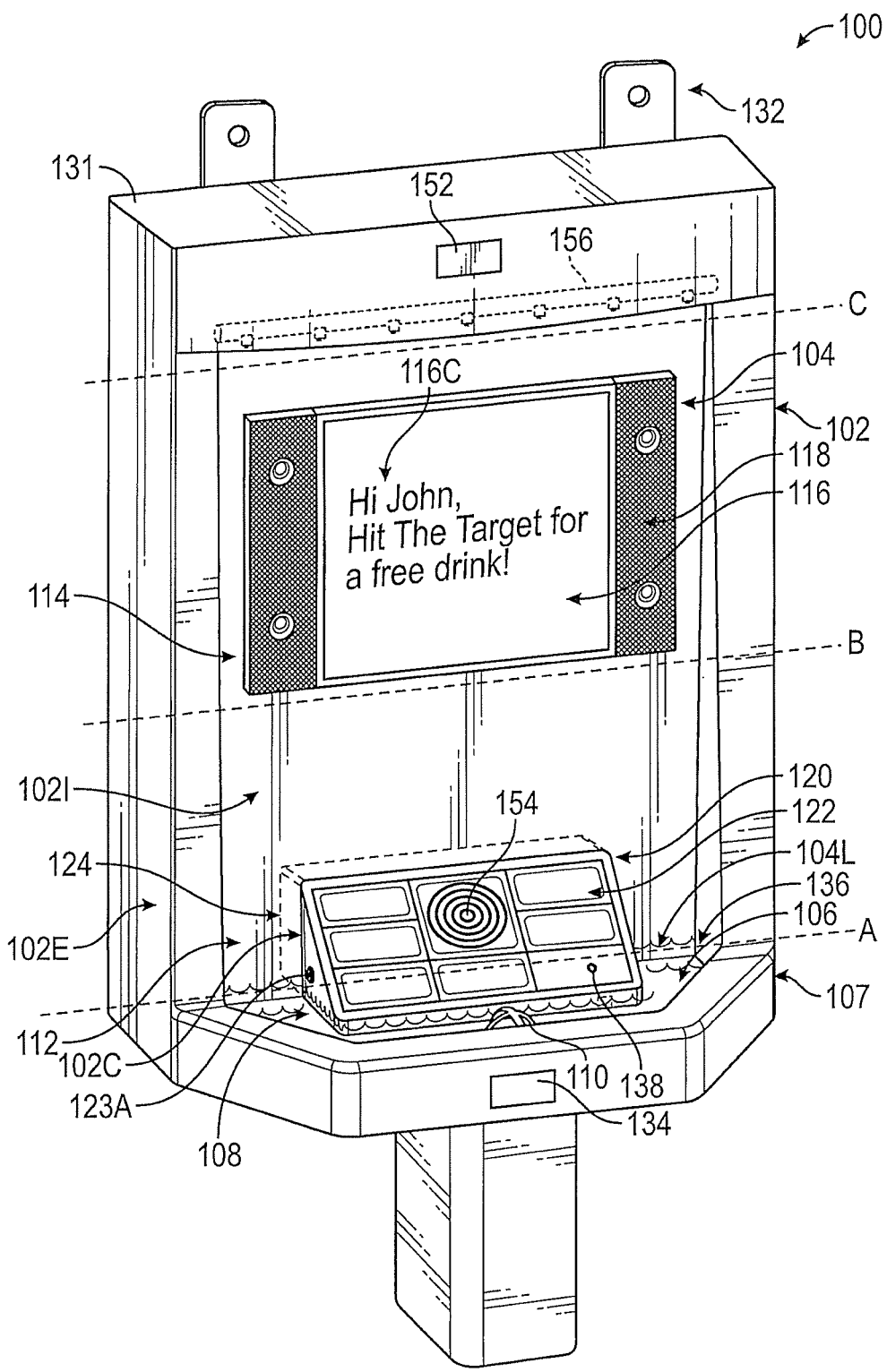
FIG. 1 shows a perspective view of an example smart urinal, according to an embodiment.

FIG. 1 shows a smart urinal 100 according to an example embodiment of the present disclosure. The smart urinal 100 may have a body 102 having an interior part 102I and an exterior part 102E. The body interior part 102I may include a recessed back portion 104 and a projecting portion 106 that extends from the recessed back portion 104 at a lower side 104L thereof. The projecting portion 106 may be circumscribed by a lip 107 of the body 102.

For the purposes of illustration, the body interior part 102I is divided into three zones: a bottom zone A, a middle zone B, and a top zone C. The bottom zone A may include the projecting portion 106 and a part of the back portion 104 (collectively, a fluid drainage area 108) and have a drain 110. The middle zone B may be adjacent (e.g., above) the bottom zone A and may include at least a part of the back portion 104 which, in a standard urinal, is configured to directly receive urine from a user (herein, a fluid receiving area 112). Top zone C, which may also include a part of the back portion 104, may be adjacent (e.g., above) the middle zone B and comprise an auxiliary area 114. While the urinal 100 is shown as having a particular shape in the figures, the artisan will understand from the discussion herein that the shape of the urinal 100 in the figures is merely exemplary and is not intended to be independently limiting. For example, in an embodiment, the smart urinal may be devoid of the auxiliary area, and may include a fluid drainage area and a fluid receiving area that are respectively smaller than the fluid drainage area 108 and the fluid receiving area 112 shown in the figures. Or, for example, the urinal 100 may be an open air urinal, a wall or floor mounted community urinal, etc. In some embodiments, the appearance (e.g., color, shape, etc.) of the smart urinal may correspond or relate to the commercial establishment within which the urinal is located (for instance, if the smart urinal is situated within a sports bar, the urinal may be configured to resemble a portion of a keg). Thus, the smart urinal (e.g., the smart urinal 100) may take on one of any multitude of shapes, and any urinal, whether now known or subsequently developed, may be converted to a smart urinal in line with the teachings of the present disclosure. For example, and as discussed herein, a prior art urinal may be retrofitted (e.g., temporarily or permanently) to serve as the smart urinal 100.

The urinal body 102, in a currently preferred embodiment, is constructed primarily of stainless steel (e.g., heavy gauge type 304 stainless steel, type 316 (or marine grade) stainless steel, etc.), as stainless steel is resistant to corrosion and can be easily cleaned. In other embodiments, the body 102 may instead be made of other metals or non-metals (e.g., ceramics, porcelain, glass, polymers, etc.).

The auxiliary area 114 may include a primary display 116. The primary display 116 may be secured to the back portion 104 of the body interior part 102I (e.g., using waterproof adhesive, waterproof fasteners, and/or other mounting arrangements). The primary display 116 may be waterproof and/or may be enclosed in a waterproof housing (e.g., a glass case). The display 116 may be an LCD display, an LED display, a HD display, a 3D display (e.g., a glasses-free 3D display), a 4K display, or any other display (e.g., a display having touch screen capability) whether now known or subsequently developed. In an embodiment, the display 116 may comprise smart glass (i.e., glass whose light transmission properties are altered when energy (e.g., voltage, light, heat, etc.) is applied thereto); for instance, the primary display 116 may be a waterproof organic light emitting diode (OLED) display. In some embodiments, the primary display 116 may be configured to be remote controlled and primary display content 116C displayed on the primary display 116 may be fed to the display 116 over a wireless network. Alternately, or in addition, an investigative computer, discussed further below, may serve to control the operation of the primary display 116.

The auxiliary area 114 may also include waterproof speakers 118. The speakers 118 may be communicatively coupled (e.g., via wires or over a wireless network) to the primary display 116. In an embodiment, the speakers 118 may be adjacent the primary display 116 (e.g., one speakers 118 may be secured to the back portion 104 at one side of the primary display 116 and another speaker 118 may be secured to the back portion 104 at an opposing side of the primary display 116). In other embodiments, the speakers 118 may be internal to the primary display 116. In some embodiments, the primary display 116 and/or the speakers 118 may be situated elsewhere, e.g., in a different zone, outwardly adjacent (such as at the top or side of) the body exterior 102E, etc. The primary display 116 and/or the associated speakers 118 may also, in embodiments, be omitted. The size and shape of the primary display 116 and/or the speakers 118 may be configured for a particular application (e.g., the primary display in a large urinal may have a larger screen for display relative to a primary display in a smaller urinal).

The smart urinal 100 may include an analysis portal 120. The analysis portal 120 may include a sensing part 122 and an investigating part 124 (see FIG. 2). The sensing part 122 may have a housing 122H which may be removably secured to a housing 124H of the investigating part 124 (e.g., via waterproof fasteners 123A and clips 123B, or other means) such that a junction 123C between the sensing part housing 122H and the investigating part housing 124H is watertight. In some embodiments, a seal (e.g., a neoprene or other seal) 125 may be disposed between the sensing part housing 122H and the investigating part housing 124H to ensure that no fluids in contact with the sensing part 122 enter the investigating part housing 124H.

The sensing part 122 may include a fluid accepting portion 126 having an upper surface 126U. The fluid accepting portion 126, as discussed herein, may be configured to accept fluids (e.g., urine of a user, water, cleaning compounds, etc.). More particularly, the fluid accepting portion 126 may include one or more fluid sensing regions 128. For example, and as shown in FIG. 2, the fluid accepting portion 126 of the sensing part 122 may include fluid sensing regions 128A-128H.

Figure 2:
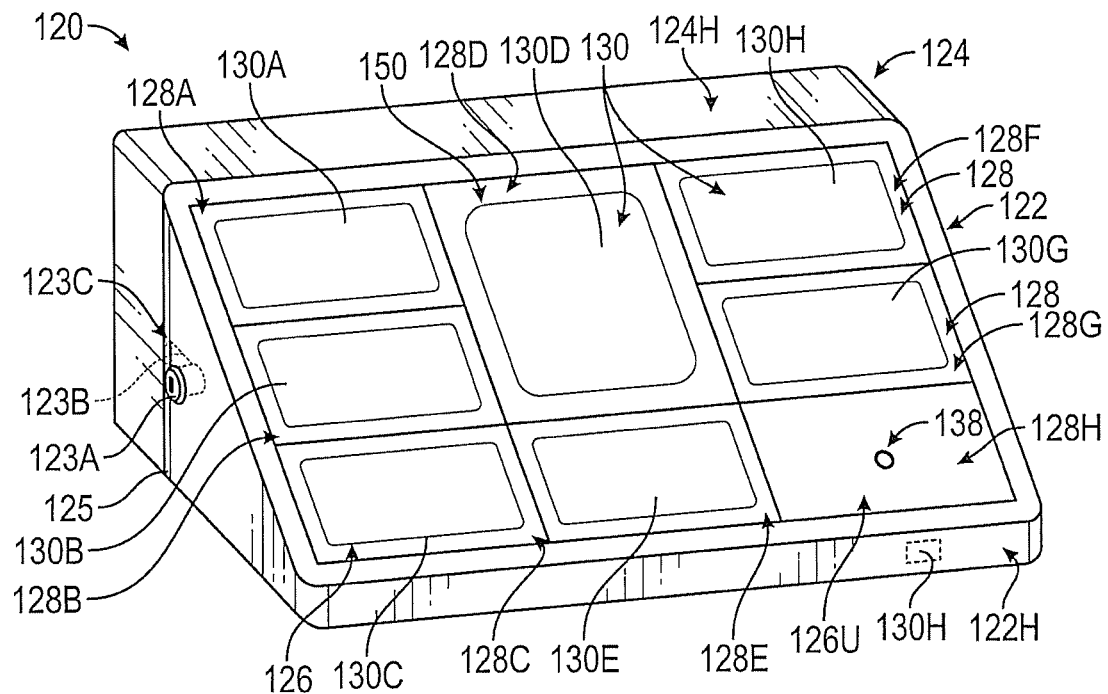
FIG. 2 shows a perspective view of an analysis portal of the smart urinal of FIG. 1.
Figure 3:
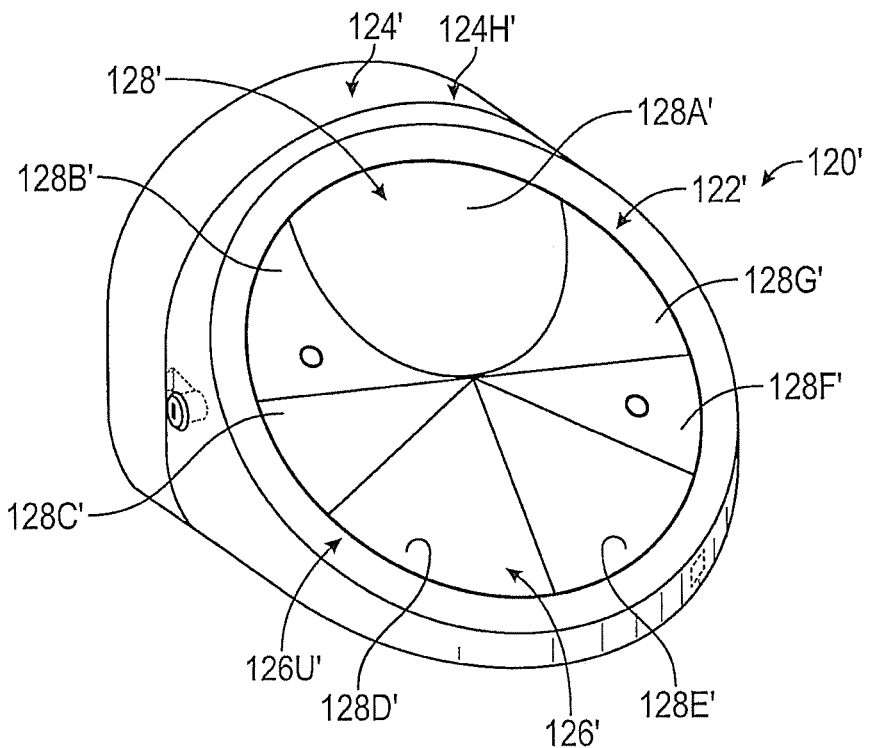
FIG. 3 shows a perspective view of an alternate embodiment of the analysis portal of FIG. 2.

In the embodiment shown in FIGS. 1 and 2, the sensing part housing 122H is generally in the shape of a triangular prism, the investigating part housing 124H coupled thereto is generally in the shape of a rectangular cuboid, and the upper surface of each of the eight fluid sensing regions 128A-128H is generally rectangular. Such, however, is merely exemplary. The analysis portal 120 (e.g., each of the sensing part 122, the investigating part 124, the sensing regions 128, etc.) may, in embodiments, take on other regular or irregular shapes, and any number of fluid sensing regions 128 (e.g., one, two, fifty, hundred, etc.) may be provided on the fluid accepting portion 126. For example, FIG. 3 shows an alternate embodiment 120' of the analysis portal 120 having seven fluid sensing regions 128A'-128G'; as can be seen, in this embodiment, an upper surface 126U' of the fluid accepting portion 126' is generally circular, the investigating part housing 124H' is generally cylindrical, and the fluid sensing regions 128A'-128G' are triangular or take on other symmetrical and non-symmetrical shapes. Thus, it will be appreciated that the analysis portal (e.g., the analysis portal 120) may take on any shape. In embodiments, the fluid accepting portion 126 of the analysis portal 120 may be configured to contact fluids directly (e.g., is configured to directly accept urine voided by a user).

Urine is a complex biofluid. Studies indicate that urine of humans may include over 3,000 detectable compounds and other substances. A healthy adult having a normal fluid intake of about 2 liters a day typically has a daily urine output of between 800 to 2,000 milliliters. Approximately 95% of a healthy individual's urine is water. The remainder may consist of solutes (i.e., chemicals which may be dissolved in water). Some of the solutes may be the result of normal or abnormal biochemical activity within the cells of the human body, whereas other solutes may be due to chemicals that originated outside the body (e.g., pharmaceutical or other drugs). In general, the solutes within the urine of a healthy individual may be classified into two groups—organic molecules, and ions. The organic molecules may be electrically neutral and may be larger in size relative to the ions. These organic molecules may include, for example, urea, creatinine, uric acid, enzymes, hormones, carbohydrates, etc. The ions in the urine are either positively or negatively charged, and may include, for example, Sodium ($Na^+$), Potassium ($K^+$), Magnesium ($Mg^{2+}$), Calcium ($Ca^{2+}$), Ammonium ($NH_4^+$), Sulfates ($SO_4^{2-}$), Phosphates ($H_2PO_4^-$, $HPO_4^{2-}$, $PO_4^{3-}$), etc.

The skilled artisan understands that analysis of the urine of an individual, including of the constituents thereof, can offer key insights about the individual's short-term and long-term health and overall well-being. For example, the skilled artisan appreciates that sugars are discharged in a healthy individual's urine at no more than 50 mg/dl. In diabetics, however, this number may increase to several hundred mg/dl, and even several thousand mg/dl. Thus, exorbitant amounts of sugar or ketones in one's urine may indicate that the individual is diabetic and/or that his kidneys are damaged or diseased. Similarly, the presence of the Leukocyte Esterase enzyme in one's urine may indicate that the individual is currently suffering from a urinary tract infection. An abnormally high specific gravity of an individual's urine may indicate that the individual is currently dehydrated. Presence of Bilirubin in one's urine may suggest liver disease. Presence of large amounts of proteins in a person's urine may indicate that the person has proteinuria. Presence of blood or myoglobin in the individual's urine may indicate that the individual suffers from hematuria. An upward trending alcohol content of the urine may indicate that the user is continually consuming alcoholic beverage(s). And so on. Indeed, the skilled artisan appreciates that the appearance (e.g., color) of the urine, its pH, its volume, its contents, its concentration, its temperature, its smell, the pressure at which it is voided and its flow rate, etc., may all provide valuable insights into an individual's health and well-being.

Typically, urinalysis is conducted in a lab. For example, an employer screening a potential employee for recreational drugs may send the employee to a lab for urinalysis. A sports team may require its players to go to a lab for urinalysis and the screening of performance enhancing drugs. A patient having back pain may likewise be ordered by a doctor to go to a lab for urinalysis. Such may inconvenience the test taker (e.g., a person may have to take several hours out of his day to drive to a lab for the testing of a sample of his urine). Because of this inconvenience, and the costs associated with the lab urinalysis, even the health conscious individuals of today generally have their urine analyzed only when required to do so (e.g., once every year, once every two years, etc.). Since urinalysis may provide key insights into an individual's health and well-being, it may be desirable to provide individuals the opportunity to have their urine tested more regularly and conveniently. It may also be desirable to securely store results of these tests and to provide the test taker individualized and real-time and/or near-time feedback based on the results of the urinalysis. The smart urinal 100 may provide for such.

Returning now to FIG. 2, each of the fluid sensing regions 128A-128H of the analysis portal sensing part 122 may include a contact or non-contact sensor 130. The sensors 130 may be temperature sensors, pressure sensors, color sensors, pH sensors, conductivity sensors, blood alcohol sensors, bacteria sensors, olfactory sensors (e.g., conducting polymer sensors), other biosensors (i.e., devices that convert a biological response, here the urine of a user, into an electrical signal), and/or any other sensors used for "lab-on-a-chip" applications, whether now known or subsequently developed. Each sensor 130 may be configured to sense and/or determine (e.g., quantitatively or qualitatively) a characteristic in the urine of an individual.

Additionally, or alternately, the analysis portal 120 of the urinal 100 may include gesture sensors. For obvious security reasons, the gesture sensors may not be able to detect crisp pictures, but rather the gesture sensors may be configured to recognize abstract movement of an individual for the purpose of generating a controlled response. In an embodiment, the gesture sensors can sense movement of an individual (e.g., a hand wave) and in response, may project an image in the urinal 100 according to the methods described herein. In another embodiment, the gesture sensor may be able to distinguish between gestures for the purpose of generating multiple controlled responses. For example, a legend describing the different recognized gestures (e.g., hand wave, movement of hand in a circle, swipe from right to left and/or left to right, etc.) may be placed on the wall in the restroom, or projected into the body of the urinal 100 as described herein, or otherwise presented to the user such that the user is familiar with the operating parameters of the gesture sensor. Each recognized gesture may be associated with a respective controlled response. For example, when the gesture sensor recognizes a hand wave, the urinal 100 using methods described herein and/or methods known to those of skill in the art, may communicate with other devices in an establishment (e.g., the establishment's computer system) to order a drink. The drink may thus be delivered by the time the user returns to his seat. When the gesture sensor recognizes a swipe from left to right and/or right to left, the sensor may communicate with programming controlling a content projector to change the content that the user is seeing, or controlling a speaker playing music to change the music. The gesture sensor may additionally, or alternately, be configured to work in conjunction with a game (described below) such that movement of the individual allows the user to interact with the game. If the user "wins," he may be rewarded with coupons (e.g., electronic codes sent to a mobile device) for free or reduced-price merchandise. Those of skill in the art will recognize that the gesture sensors may be configured to sense and provide controlled responses beyond those described herein.

In an embodiment, the fluid sensing regions 128A-128H may include sensors 130A-130H, respectively. The sensors 130A-130H may be disposed on the upper surface 126U of the fluid accepting portion 126, may be embedded in the upper surface 126U, and/or may be underneath the upper surface 126U. For instance, as shown in FIG. 2, and only by way of example, sensors 130A-130G may be disposed on the upper surface 126U of the fluid accepting portion 126 or be embedded therein, and sensor 130H may be underneath the upper surface 126U of the fluid accepting portion 126 of the sensing part 122. The investigating part 124 may be communicatively (e.g., electronically via wires or wirelessly) coupled to the sensing part 122. As discussed herein, the investigating part 124 may evaluate the readings taken by the one or more sensors 130A-130H, and may generate one or more outputs in response.

The analysis portal 120 may be disposed (e.g., secured or otherwise situated) within the urinal body interior 102I such that an individual can urinate on the fluid accepting portion 126 directly. For example, and as shown in FIG. 1, the body interior 102I (and more specifically, the back portion 104) may include a cutout 102C, and the analysis portal 120 may be situated within the body interior 102I such that at least a part of the fluid accepting portion 126 of the sensing part 122 is in front of the back portion 104 and the cutout 102C and at least a part of the investigating part 124 is behind the back portion 104 and the cutout 102C. As can be seen, the fasteners 123A may be accessible while the urinal 100 is configured for use (e.g., is secured to a wall via hooks 132 (FIG. 1) and fasteners (not shown), or other means). Thus, the sensing part housing 122H (and the sensing part 122 housed therein) may be uncoupled from the investigating part housing 124H (e.g., for maintenance, cleaning, etc.) without the need to dismantle the urinal 100. In embodiments, the analysis portal 120 may be modular such that the sensing part 122 of one analysis portal 120 may be removed therefrom and be communicatively coupled to the investigating part 124 of another analysis portal 120.

When the analysis portal 120 is situated within the body interior 102I, the sensing part 122, and specifically the upper surface 126U of the fluid accepting portion 126 thereof, may be angled with respect to the horizontal. For example, the upper surface 126U may make a 135 degree, a 150 degree, or a different angle with respect to the horizontal. This may allow urine voided on an upper portion of the upper surface 126U (e.g., urine voided on the fluid sensing regions 128A, 128D, and 128F) to gradually flow down the upper surface 126U and fall eventually into the fluid drainage area 108 by virtue of gravity. The gradual flow of the urine from the upper surface 126U down into the fluid drainage area 108 may allow sensors 130 adequate time to measure various characteristics of the urine, as discussed herein. In other embodiments, however, and depending on the particular application, the upper surface 126U of the fluid accepting portion 126 may be generally perpendicular to the horizontal.

In an embodiment, the sensors 130 may be disposed at strategic areas within the sensing part 122 such that the urine of a user voided on the fluid sensing region 128D is automatically persuaded to reach the remaining fluid sensing regions 128A-128C and 128E-128H before the urine exits through the drain 110. For example, the upper surface 126U of the fluid accepting portion 126 may be slightly convex, or a web of channels may be provided on the upper surface 126U such that urine voided on the fluid sensing region 128D reaches the other fluid sensing regions 128A-128C and 128E-128H. In some embodiments, one or more of the sensing areas 128A-128H may include pits or other indentations to retain fluids (e.g., the urine of a user, water, cleaning compounds, etc.) temporarily before they are flushed out the drain 110. In other embodiments, pits and/or channels may be etched into the back portion 104 of the urinal body 102 (e.g., etched into the stainless steel back portion 104), and the sensors 130A-130H may be disposed within these pits. Thus, the analysis portal 120, and specifically the sensing part 122 thereof, may be configured in one of any number of ways so long as urine voided on a particular portion of the sensing part 122 (e.g., on the fluid sensing region 128D) is persuaded to flow to other portions of the sensing part 122; such may allow multiple sensors 130 to measure different characteristics of a solitary urine sample.

Another factor that may be taken into consideration when disposing the sensors 130 in strategic areas within the sensing part 122 situated in the urinal 100 is the amount of cleaning required by these sensors 130 to make accurate (or relatively accurate) measurements. For instance, remnant urine from a prior user may adversely affect (e.g., cause to be inaccurate) the readings of a sensor for detecting the presence of drugs in a urine sample more so than the readings of a temperature sensor. Thus, the sensors 130 may be situated within the urinal body interior 102I such that the sensors 130 that require the most cleaning are situated in areas most likely to be more thoroughly cleaned upon "flushing". In some embodiments, the urinal 100 may have automatic flushing capability (e.g., a proximity detector 134 (such as an infrared or other suitable sensor, see FIG. 1) may detect that a user is no longer in front of the urinal 100, and the flushing mechanism may resultantly be activated). When the flushing mechanism is activated, water may flow down from top zone C (e.g., through an opening in the upper side of the back portion 104) down to the middle zone B, and ultimately to the bottom zone A. This water may, in general, get dirtier as it makes its way from the top zone C to the bottom zone A (i.e., urine within the urinal body 102 may mix with the water as it makes its way down to the drain 110). Hence, in an embodiment, the sensors 130 associated with the sensing regions 128A, 128D, and 128F (which, in the illustrated embodiment, are upstream from the other sensing regions 128 and may generally receive the cleanest water upon flushing) may be those sensors 130 for which cleanliness and wash-down predictability is most important.

When conducting urinalysis, measurement of certain characteristics may require that the urine be diluted (e.g., with water or another substance) before testing. In some embodiments, thus, one or more of the fluid sensing regions 128, including the sensors 130 associated therewith, may be disposed within the fluid drainage area 108. For example, and with reference to FIGS. 1 and 2, sensors 130C, 130E, and 130H may be situated within the urinal body interior 102I such that they are below water line 136. Such configuration may ensure that the sensors 130 below the water line 136 receive a diluted sample of urine for testing.

Figure 4A:
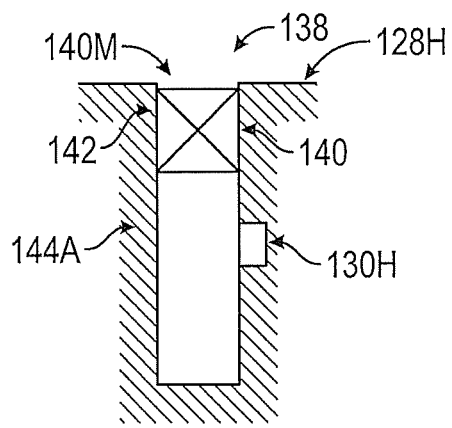
FIGS. 4A-4C schematically illustrate the workings of a plunger associated with a sensor of the analysis portal of FIG. 2.
Figure 4B:
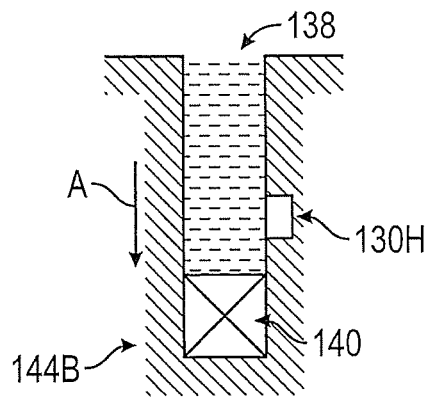
Figure 4C:
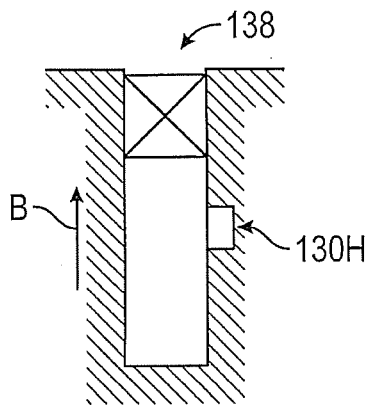

As noted above, the sensing part 122 includes sensors 130 (e.g., sensors 130A-130H) that are disposed on, embedded within, or situated below the upper surface 126U of the fluid accepting portion 126. Those sensors 130 that are below the upper surface 126U of the fluid accepting portion 126 (e.g., sensor 130H) may, in embodiments, test the fluid (e.g., undiluted urine, urine diluted with water or another substance, etc.) after it has been drawn into a tube or other container below the upper surface 126U. Pores (e.g., pore 138, see FIG. 2) may be provided on the fluid accepting portion upper surface 126U to allow for a sample to be drawn into the tube and pushed out therefrom after analysis. FIGS. 4A-4C show the example sensor 130H in more detail.

Specifically, FIG. 4A shows the fluid sensing region 128H having the pore 138. A tube 140 having a mouth 140M may extend downward from the fluid accepting portion upper surface 126U. The mouth 140M of the tube 140 may be adjacent the upper surface 126U, and specifically, adjacent the pore 138 to allow for a sample of fluid to be drawn into the tube 140. In an embodiment, the tube 140 may have a plunger 142, which is shown in a first position 144A in FIG. 4A. In the first position 144A, the plunger 142 may seal the mouth 140M and thereby preclude fluid (e.g., urine) from entering the tube 140 through the pore 138. When testing of a sample is to be conducted, the plunger 142 may move from the first position 144A in direction A to a second position 144B, as shown in FIG. 4B. Movement of the plunger from the first position 144A to the second position 144B may cause fluid (e.g., urine) to be drawn into the tube 140 via the pore 138. The sensor 130H may test the fluid sample while the sample is within the tube 140. Thereafter, as shown in FIG. 4C, the plunger 142 may move in a direction B back to its first position 144A, which may cause the sample to be pushed out of the tube mouth 140M and through the pore 138 back to the fluid accepting portion upper surface 126U (at which point it may start to flow towards the drain 110). This configuration may ensure that a specific known volume of fluid is provided to the sensor 130H for testing. In some embodiments, after the urine sample within the tube 140 has been tested using the sensor 130H and pushed out the tube 140, and before another urine sample is tested, the tube 140 may undergo a cleanup process. Specifically, after the urine sample is pushed out the tube 140, the plunger 142 may move back from its first position 144A to its second position 144B to draw in water (or cleaning fluids, as discussed below), and thereafter, move back to its first position 144A to push the water out the tube 140. Movement of the plunger 142 may be effectuated by an electromechanical (e.g., a motor), hydraulic, or other system, the operation of which may be controlled by the investigative computer (discussed further below).

In embodiments, the analysis portal 120, and specifically the sensing part 122 thereof, may include a secondary display 150. In the illustrated embodiment, the secondary display 150 is situated in the fluid sensing region 128D. Of course, in other embodiments, the secondary display 150 may be situated elsewhere within the urinal 100 or may be omitted. In some embodiments, the secondary display 150 may extend along the entire upper surface 126U of the fluid accepting portion 126. Like the primary display 116, the secondary display 150 may be an LCD display, an LED display, a HD display, a 3D display (e.g., a glasses-free 3D display), a 4K display, an OLED or other smart glass display, or any other display (e.g., a display having touch screen capability) whether now known or subsequently developed. The secondary display 150 may be waterproof, and may be embedded within or disposed atop the fluid accepting portion upper surface 126U.

To illustrate the workings of the smart urinal 100, a non-limiting example is detailed below. In this example, the sensors 130 are configured as follows: the sensor 130A is configured to detect the presence of drugs (e.g., illicit recreational drugs, performance enhancing drugs, pharmaceuticals, etc.) within a urine sample (i.e., within the urine on the fluid sensing region 128A), the sensor 130B is configured to measure protein content in the urine, the sensor 130C is a color detector (e.g., an optical sensor), the sensor 130D is a pressure sensor (i.e., the fluid sensing region 128D may include both a pressure sensor 130D and the secondary display 150), sensor 130E is a blood alcohol content sensor, sensor 130F is a sugar (e.g., glucose) sensor, sensor 130G is a temperature sensor, and the sensor 130H is a biosensor configured to determine the presence of one or more bacteria within the urine. The artisan will appreciate that this delineation of the particular sensors 130A-130H is merely exemplary and is not intended to be independently limiting. Indeed, any sensor (e.g., an optical sensor, a potentiometric biosensor, an amperometric biosensor, a nanosensor (such as carbon nanotube sensor systems and wireless grapheme nanosensor systems), an olfactory sensor, a spectroscopic sensor, an array sensor (e.g., a laser grid refraction array measuring optical gradient based on molecular structure of the urine), etc., whether now known or subsequently developed, which can be used to sense a characteristic in a urine sample, may be employed in the smart urinal 100.

Figure 5:
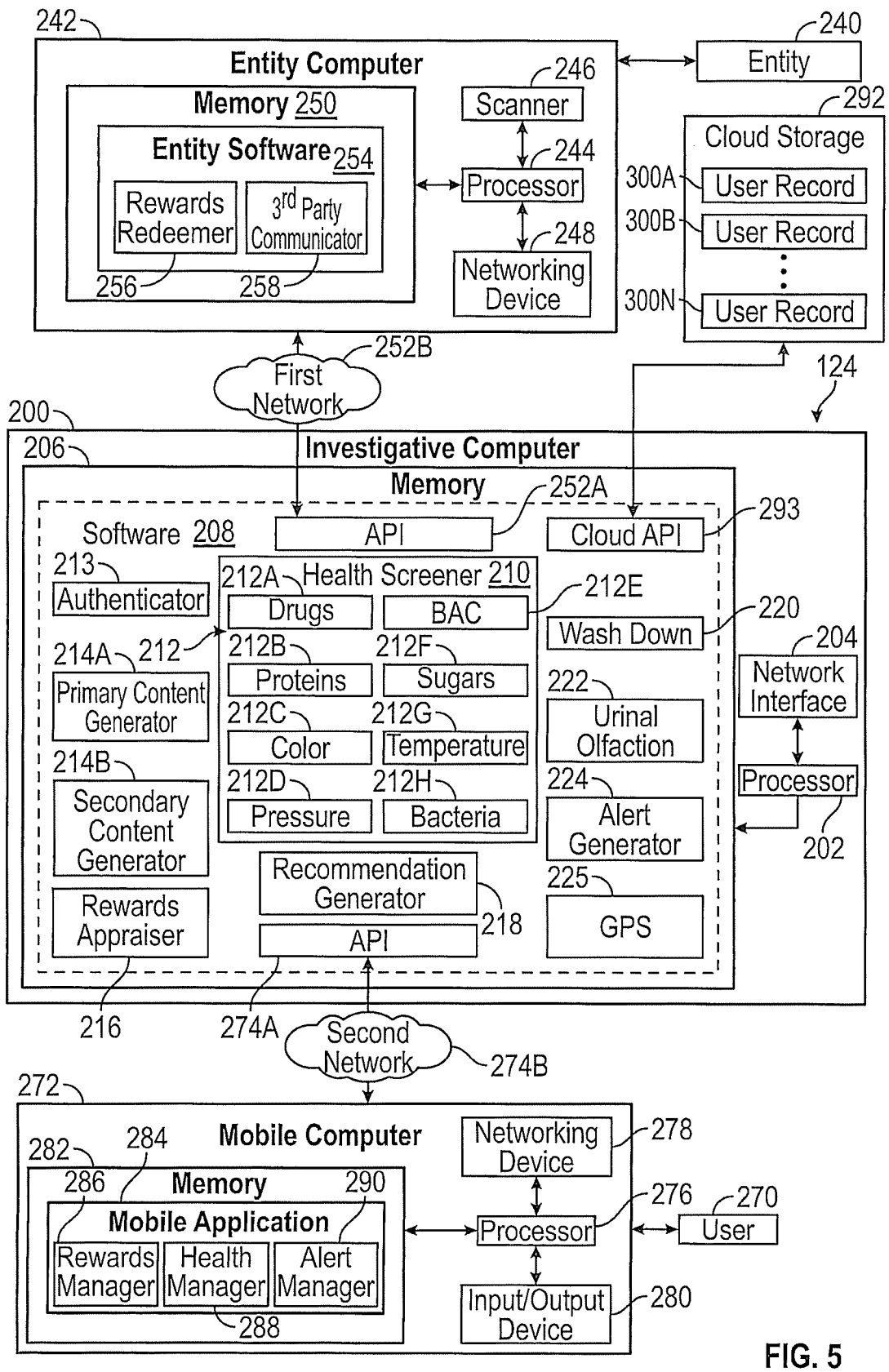
FIG. 5 schematically illustrates an investigative computer of the analysis portal of FIG. 2 and outlines communication between it and other computing devices.

Focus is now directed to FIG. 5. This figure schematically illustrates the investigating part 124 of the analysis portal 120, which, as noted above, is communicatively coupled to the sensing part 122 (e.g., to the sensors 130A-130H). The investigating part 124, in this example, is configured to evaluate the readings obtained by the one or more sensors 130A-130H, and may communicate with the user and others in response to said evaluation.

The example investigating part 124 includes an investigative computer 200. The investigative computer 200 includes a processor 202 communicatively coupled to a network interface 204 and memory 206. Processor 202 represents one or more digital processors. In some example embodiments, the processor 202 may be configured through particularly configured hardware, such as an application specific integrated circuit (ASIC), field-programmable gate array (FPGA), etc., and/or through execution of software to perform functions in accordance with the disclosure herein. Network interface 204 may be implemented as one or both of a wired network interface and a wireless network (e.g., Wi-Fi, Internet, Bluetooth, etc.) interface, as is known in the art. Memory 206 represents one or more of volatile memory (e.g., RAM) and non-volatile memory (e.g., ROM, FLASH, magnetic media, optical media, etc.). Although shown within the investigative computer 200, memory 206 may be, at least in part, implemented as network storage that is external to the analysis portal 120 and accessed via network interface 204.

Software 208 may be stored in a transitory or non-transitory portion of the memory 206. Software 208 includes machine readable instructions that are executed by processor 202 to perform the functionality of the investigating part 124 as described herein. In the illustrated example, the software 208 contains a health screener 210, an authenticator 213, a primary content generator 214A, a secondary content generator 214B, a rewards appraiser 216, a recommendation generator 218, a wash-down module 220, a urinal olfaction module 222, an alert generator 224, and a global positioning system 225, each of which are described in more detail below.

The health screener 210 may be configured to evaluate the readings obtained from the sensors 130. Specifically, the health screener 210 may have a module 212 (e.g., code to implement one or more routines) associated with each of the sensors 130. For instance, in the illustrated embodiment, since the sensors 130A-130H are configured to respectively sense and/or detect drugs, proteins, color, pressure, blood alcohol content, sugars, temperature, and bacteria of or within the urine, the health screener 210 may include a drugs module 212A, a protein module 212B, a color module 212C, a pressure module 212D, a blood alcohol content module 212E, a sugars module 212F, a temperature module 212G, and a bacteria module 212H. Each module 212 may be configured to evaluate the particular reading obtained by the associated sensor 130 to determine whether the characteristic being evaluated is normal or is cause for alarm. For example, one or more of the modules 212 may, in embodiments, include or have access to memory (e.g., memory 206) containing average (i.e., normal) values for the particular characteristic being evaluated. For instance, and as discussed above, sugars are discharged in a healthy individual's urine at no more than 50 mg/dl. The sugars module 212F associated with the sugar sensor 130F may therefore have this threshold value 50 mg/dl stored thereon or otherwise accessible thereto, so that when the urine of a user is tested, the sugars module 210F of the investigating part 124 can evaluate whether the sugar level thereof is normal or is a cause for alarm. For example, if the sugar sensor 130F determines that the quantity of sugars in the urine sample is 25 mg/dl, the sugars module 210F may determine that the urine of the user does not contain excessive sugars. Alternately, if the sugar sensor 130F determines that the quantity of sugars in the urine sample is 300 mg/dl, the sugars module 210F may determine that the user's urine contains excessive sugar. As another example, where the drugs module 212A is intended to determine the presence of marijuana in the urine, the drug module 212A may have access to information outlining that a non-zero value for THC-COOH, a non-psychoactive marijuana metabolite, indicates that the user recently used marijuana. And so on. As discussed herein, the investigating part 124 may take action based on the evaluation of the one or more readings obtained from the sensors 130.

The software 208 may include an authenticator 213. The authenticator 213 may, in embodiments, communicate with a mobile computer of a user (discussed further below) to verify the identity of the user. For instance, and as discussed below, a user may download a mobile application to allow him to interact with the smart urinal 100. During the installation process, a unique number associated with the user's mobile computer (e.g., an Android ID, a Google Advertising ID, a Universal Device ID, etc.) may be retrieved and stored (e.g., in cloud storage 292, discussed below). When the proximity detector 134 (see FIG. 1) indicates that a user is proximate (e.g., within 1-24 inches of) the urinal 100, the authenticator 213 may use the network interface 204 to interact with the user's mobile computer (e.g., over a Bluetooth or other network) to determine the device ID of the user's mobile computer. The authenticator 213 may thereafter match the device ID obtained when the user is at the urinal 100 with the device ID retrieved during the mobile application installation, and thereby, identify and authenticate the user. Alternately, or in addition, in some embodiments, the smart urinal 100 may include a biometric sensor 152 (see FIG. 1, e.g., a device that scans the iris, fingerprints, facial features, handwriting, etc.) of the user. In these embodiments, the user may provide a biometric sample upon installation of the mobile application, and the authenticator 213 may compare and match same to the sample provided by the user at the urinal 100 to authenticate the identity of the user. Still further, the smart urinal 100 may further include gesture sensors as described above. Here, the user may gesture in some manner, which may allow for interaction with and/or control of other elements (e.g., the primary content generator 214A, the secondary content generator 214B, etc.).

The primary content generator 214A may generate content (e.g., content 116C, see FIG. 1) for display on the primary display 116. The primary display content 116C may be general content or individualized (i.e., personalized) content. General content, as used herein, may include TV channels, sports games, movies, non-targeted advertisements, etc. Individualized content, as used herein, may include a personalized message, targeted advertising, or any other content that is tailored to the particular user using the urinal 100. In an embodiment, when the urinal 100 is not in use, the content 116C displayed on the primary display 116 may be general content. When a user walks up the urinal 100 and his identity is confirmed using the authenticator 213, or a particular gesture is recognized via the gesture sensor, the primary content generator 214A may cause the primary display 116 to display content 116C that is personalized to that user. For instance, where the user provides his name as part of the installation of the mobile application to interact with the urinal 100 (discussed further below), upon identification of the user at the urinal 100 via the authenticator 213, the primary content generator 214A may cause the primary display 116 to display an individualized message that includes the name of the user. Alternately or in addition, during installation of the mobile application, the user may pick topics that are of interest to the user, and the primary display 116 may display personalized content (e.g., targeted advertisements, movie trailers, etc.) in line with the user's preferences. In some embodiments, the personalized content may be dynamic (e.g., where the user used a search engine on the mobile device to search for listings for a new vehicle within the last hour, the primary content generator 214, upon communication of the mobile device with the software 208, may display advertisements for new vehicles). The user may gesture (e.g., move hand from right to left) to change channels or otherwise alter the content on the primary display 116. The primary display 116 may thus, in embodiments, provide the user a personalized and immersive experience at the urinal 100.

The secondary content generator 214B may generate content 154 (see FIG. 1) for display on the secondary display 150. For example, in some embodiments, the secondary content generator 214B may cause content 154 (specifically, target indicia as shown in FIG. 1) to be generated and displayed on the secondary display 150 when the proximity sensor 134 indicates that a user is about to use the urinal 100. Alternately, the secondary content generator 214B may cause content 154 to be displayed on the secondary display 150 at all times. The target indicia 154 may encourage the user to void his urine directly onto the fluid sensing region 128D, so that: (a) the pressure at which the urine is voided may be measured by the pressure sensor 130D; and (b) at least a portion of the urine volume reaches the other sensors 130A-130C and 130E-130H before the urine flows out the drain 110. While the target indicia 154 shown in FIG. 1 includes concentric circles, the artisan will appreciate that any other indicia may likewise be provided (e.g., the secondary content generator 214B may cause the secondary display 150 to display the words "aim here"; or, for instance, flying targets (as in skeet shooting) may appear on the secondary display 150 to encourage the user to void his urine directly onto the fluid sensing region 128D). In some embodiments, the secondary content generator 214B (and/or the primary content generator 214A) may allow the user to interact with the smart urinal 100 in real-time; for example, the content 154 (or the content 116C) may change colors (e.g., change from blue to green) as the user voids his urine on the fluid sensing region 128D. Or, for instance, virtual bowling pins displayed on the secondary display 150 may appear to fall as the user voids his urine on same.

Typically, because of the inconvenience and time commitment, consumers are wary of taking polls. As noted above, however, many members in a given community will be required to use a urinal several times a day. Based on this realization, in some embodiments, the content 154 displayed by the secondary content generator 214B on the secondary display 150 may include one or more polls. For example, the secondary content generator 214B may display the names of two or more movies and ask the user to indicate the movie he is more likely to see by voiding his urine on same. Or, for example, the secondary content generator 214B may display the names and/or images of two or more retail items and ask the user to indicate the item he likes less by voiding his urine on same. This polling data may be stored in the cloud (discussed below) and may, in embodiments, be sold to interested parties. Particularly where many (e.g., ten, hundred, thousand, etc.) smart urinals are installed in a region (e.g., in a country, in a continent, etc.), the polling data may indicate societal trends and be an impetus for change (e.g., if ninety percent of smart urinal users indicate that they do not like a particular policy implemented by a politician, the politician may change his stance on the policy based on the polling results). In some embodiments, the polling questions may instead be displayed on the primary display 116, and the investigative computer 200 may determine the user's response in other ways (e.g., the user may look at an option, and eye tracking software associated with the urinal 100 may track the user's eyes to determine the intended response; or the user gestures and gesture sensors and associated urinal software may determine the intended response).

In some embodiments, the rewards appraiser 216 may cause the user to be given a reward based on the urinalysis. For example, where the pressure sensor 130D indicates that the user voided his urine on (or primarily on) the fluid sensing region 128D, the rewards appraiser 216 may reward the user. Or, for instance, the rewards appraiser 216 may offer the user a reward where the urinalysis indicates that the user is making healthful choices (e.g., where the urinalysis indicates that the user's sugar level is low). As discussed in more detail below, the rewards may be communicated by the rewards appraiser 216 to the mobile computer of the user for redemption.

The reward may be associated with the particular establishment within which the urinal 100 is located. For instance, where the smart urinal 100 is located within a bar, the reward may be a free (or a discounted) drink. Or, for example, where the smart urinal 100 is located within a gym, the reward may be a free "flex dollar." In some embodiments, to be awarded a reward, the user may be required to take multiple trips to the urinal 100. For example, in an embodiment, the user may be required to use the urinal 100 in a bar three times (or a different number of times) during a given time period (e.g., one night) to be able to receive a reward (e.g., a discounted drink). As will be appreciated, such may encourage the user to stay at the bar longer than he had originally intended, and thereby, increase the revenues of the bar (or other establishment) within which the urinal 100 is located.

In some embodiments, the user may be allowed to use the urinal 100 to play games of skill and/or games of chance, and the reward awarded by the reward appraiser 216 may be associated with such game(s). For example, the urinal 100 may be situated within a casino, and the content displayed on the secondary display 150 (and/or the primary display 116) may include video games (e.g., slots, poker, Candy Crush, etc.). Thus, in some embodiments, the user may be allowed to gamble while he is urinating at the urinal 100. The rewards appraiser 216 may wirelessly communicate monies won by the user to the mobile computer of the user (e.g., via a digital wallet service).

In some embodiments, the investigative computer 200 may include a recommendation generator 218. The recommendation generator 218 may generate a personalized recommendation for the user based on the evaluation conducted by the health screener 210, and may take into account the establishment within which the urinal 100 is located. For example, where the urinal 100 is located within a bar and the health screener 210 indicates that the user's blood alcohol level is low, the recommendation generator 218 may recommend that the user enjoy an alcoholic beverage. Or, for instance, where the urinal 100 is located within a gym and the health screener 210 indicates that the user is dehydrated, the recommendation generator 218 may recommend that the user drink some water (and/or visit a physician). In embodiments, the recommendation generator 218 may be in communication with the primary content generator 214A and cause the recommendation to be displayed on the primary display 116. Alternately, or in addition, the recommendation may be transmitted by the recommendation generator 218 to the user's mobile computer.

The wash down module 220 may be configured to automatically flush the urinal 100 where test readings taken by the sensors 130A-130H indicate that the sensors 130 are unclean (e.g., where one or more sensors have a prior user's urine disposed thereon such that they are unable to provide accurate readings). More specifically, after one user uses the urinal 100, the automatic flushing mechanism of the urinal 100 may automatically flush the urinal 100. In the illustrated embodiment, at this point, one or more of the sensors 130A-130H may take test readings, which may be evaluated by the wash down module 220. If the sensors 130A-130H are suitably clean, the test readings may so indicate (e.g., the sugar sensor 130F may not sense any sugars because the prior user's urine has been washed off the sensor 130F via the automatic flushing). Where, however, the test readings indicate that one or more of the sensors 130A-130H are dirty, the wash down module 220 may cause the urinal 100 to be flushed again (e.g., where the sugar sensor 130F gives a non-zero reading after the urinal 100 has been flushed and before another user uses the urinal 100, the wash down module 220 may ascertain that remnants of the prior user's urine remain on the sugar sensor 130F and activate the flushing mechanism). In some embodiments, a vessel 156 containing a sanitation agent may further be provided (e.g., in the top zone A, the middle zone B, or elsewhere). In these embodiments, the wash down module 220 may also cause sanitation agent to be dispensed into the urinal 100 when the test readings indicate that one or more of the sensors 130 are unsuitably dirty.

The skilled artisan understands that various machine olfactory sensors (e.g., conductive polymer sensors, tin-oxide gas sensors, quartz-crystal micro-balance sensors, etc.) are currently available, and that much research is underway to advance the capabilities of these sensors. The urinal olfaction module 222 may include an olfactory sensor to further facilitate cleanliness of the urinal 100. Automatic flushing mechanisms of urinals of the prior art, from time to time, fail to detect a user, and consequently, fail to flush the urinal after it has been used. Moreover, these mechanisms do not ensure that all the urine dispensed within the urinal is actually cleaned off and flushed out of the urinal upon flushing. Resultantly, bad odors may permeate throughout the restroom within which the prior art urinals are located. The urinal olfaction module 222 may solve this problem. Specifically, the urinal olfaction module 222 may include an olfactory sensor (whether now known or subsequently developed) which may activate the automatic flushing mechanism when it determines that bad odors are emanating from the urinal 100. In some embodiments, the olfaction module 222 may further cause an antibacterial agent (e.g., Lysol® stored in the vessel 156) and/or fragrance to be dispensed within and around the urinal 100 based upon a determination that bad odors are emanating from the urinal 100. In embodiments, instead of, or in addition to, a fragrance that masks the bad odor(s), the agent caused to be dispensed by the olfaction module 222 upon detection of the bad odor(s) by the olfactory sensor may serve to neutralize (e.g., by chemical alteration of the urine) the bad odor(s). In some embodiments, the olfactory sensor may be remote from the urinal 100 and may be configured to communicate with the investigative computer 200 over a network.

The alert generator 224 of the software 208 may generate an alert based on the urinalysis of a user. For example, if the urinalysis indicates that the user's blood alcohol levels are dangerously high, the alert generator 224 may generate an alert. The alert may be auditory, visual, or other type of alert, and may be communicated in any number of ways. For example, in an embodiment, the alert generator 224 may display an alert message on the primary display 116 and also transmit the alert message to the mobile device of the user. In some embodiments, the alert message may also be communicated to third parties. For instance, the alert message may be communicated to the establishment within which the urinal 100 is located.

The analysis portal 120 may, in embodiments, be portable. That is, the entire analysis portal 120 may, in embodiments, be transferred from one urinal at one location to another urinal at the same or a different location. As discussed above, the sensing part 122 of the analysis portal 120 may also, in embodiments, be removed from the analysis portal 120 and be communicatively coupled to the investigating part 124 of a different analysis portal 120. The global positioning system 225 may indicate a current location of the analysis portal 120 (e.g., of the sensing part 122 or the investigating part 124 thereof).

The investigative computer 200 may be communicatively coupled to a computer of the establishment (e.g., an entity 240, see FIG. 5) with which the urinal 100 is associated. While certain commercial establishments (e.g., bars and gyms) are disclosed as examples above, the application of the urinal 100 is not so limited. Rather, the establishment (or "entity") may be any establishment (e.g., a private or public school, a non-profit or other hospital, a restaurant, an office building, a prison, an assisted living facility, etc.) within which urinals may be located. In embodiments, the smart urinal 100 may also be situated at a private residence. Thus the terms "establishment" and "entity," as used herein, encompass any structure within which urinals are or can be located.

For the purposes of illustration, consider that the entity 240 is a bar having a computer 242 (e.g., a computer linked to the cash register). The entity computer 242 may have a digital processor 244, which may be coupled to a scanner 246, a networking device 248, and memory 250. The scanner 246 may be, for example, a barcode (e.g., a one dimensional code 128 barcode or a two dimensional QR code) scanner. The networking device 248 may be configured to allow the entity computer 242 to communicate over wired and/or wireless networks; for instance, as shown in FIG. 5, the investigative computer memory 206 may have an Application Programming Interface (API) 252A, and the networking device 248 of the entity computer 242 may allow the investigative computer 200 of the smart urinal 100 to communicate with the entity computer 242 over a first network 252B (e.g., a Wi-Fi, Internet, Bluetooth, or other wired or wireless network) via the API 252A. The memory 250 may be one or more of volatile memory (e.g., RAM) and non-volatile memory (e.g., ROM, FLASH, magnetic media, optical media, network memory, etc.). In an embodiment, a transitory and/or non-transitory memory 250 of the entity computer 242 may contain entity software 254.

The entity software 254 may include machine readable instructions that are executed by processor 244 to perform the functionality of the entity computer 242 as described herein. The entity 240 may, for example, download (e.g., over the web, via a flash drive, CD, or other means) the entity software 254 upon installation of the smart urinal 100 at the entity 240.

Figure 6:
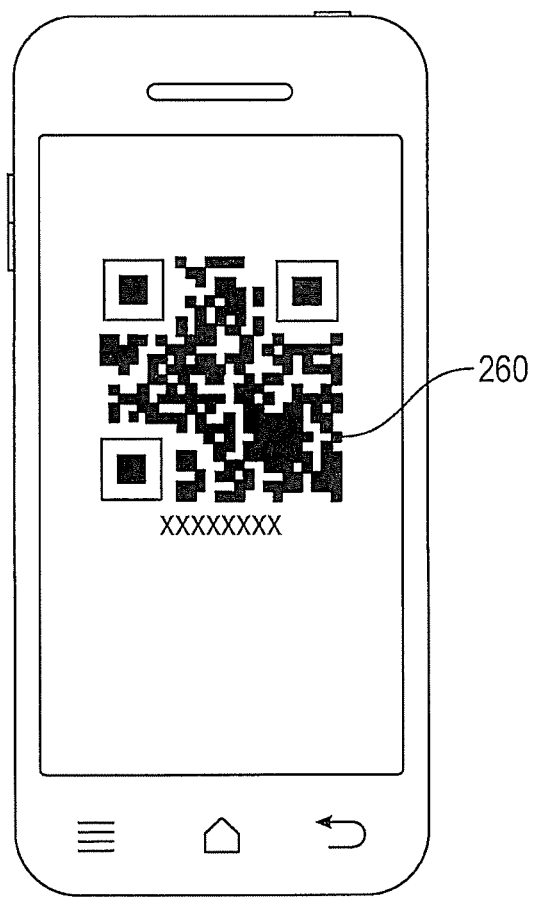
FIG. 6 shows a top view of a mobile device configured to communicate with the smart urinal.

In an embodiment, the entity software 254 may include a rewards redeemer 256 and a third party communicator 258. The rewards redeemer 256 may, in conjunction with the rewards appraiser 216 of the investigative computer 200, allow a user to redeem at the entity 240 a reward awarded to the user. For example, where the rewards appraiser 216 awards the user a free beer based on the urinalysis, the investigative computer 200 may transmit to the user's mobile computer (discussed further below) a code (e.g., QR code 260, see FIG. 6); the user may have the entity 240 scan this code 260 using the scanner 246, and the rewards redeemer 256 may inform the entity 240 that the code 260 translates to a free beer.

The third party communicator 258 may communicate with the alert generator 224, and based on this communication, may contact a third party. For example, where the alert generator 224 generates an alert because the user's blood alcohol levels are dangerously high, the third party communicator 258 may cause a cab to be called for that user. Or, for example, where the establishment is a hospital and the urinalysis indicates an alert condition (e.g., a dangerously high blood pressure), the third party communicator 258 may automatically page a physician. In some embodiments, the functionality of the third party communicator 258 may be incorporated in the alert generator 224 (i.e., in some embodiments, the alert generator 224 may directly communicate with a third party without going through the entity computer 242).

The smart urinal 100, and specifically the investigative computer 200 thereof, may further communicate with the mobile computer of a user 270 (see FIG. 5). For instance, the investigative computer 200 may communicate with a mobile computer 272 of the user 270 over a second network 274B. The second network 274B may preferably be a wireless network (e.g., a Bluetooth, Wi-Fi, or other network). In one embodiment, the first network 252B may be a wireless internet network (e.g., Wi-Fi) and the second network 274B may be a Bluetooth or a near field communication network. In another embodiment, the first network 252B and the second network 274B may be the same network.

The mobile computer 272 may be, for example, a smart phone (see FIG. 6), a laptop, a PDA, or any other portable computer whether now known or subsequently developed associated with the user 270. It is envisioned that the user may carry the mobile computer 272 on his person. In an embodiment, the mobile computer 272 may include a processor 276, which may be in data communication with a networking device 278, an input/output device 280, and memory 282. The processor 272 may be one or more digital processors. The networking device 278 may be configured to allow the mobile computer 272 to communicate with the smart urinal 100 and other computerized devices over wireless (or wired) networks. For instance, and as shown in FIG. 5, the investigative computer software 208 may have API 274A, and the networking device 278 of the mobile computer 272 may allow the mobile computer 272 to communicate over the second network 274B (e.g., a Wi-Fi, Internet, Bluetooth, or other wired or wireless network) with the investigative computer 200 via the API 274A.

In some embodiments, to interact with the urinal 100 via the mobile computer 272, the user 270 may download in the memory 282 a mobile application 284. The mobile application 284 may include machine readable instructions that are executed by the mobile computer processor 276 to perform the functionality of the mobile computer 272 as described herein.

In an embodiment, the mobile application 284 may include a rewards manager 286, a health manager 288, and an alert manager 290. The rewards manager 286 may allow the user 270 to keep track of and manage the one or more rewards that are awarded to the user 270 by the rewards appraiser 216. For example, and as discussed above, the rewards appraiser 216 may award the user a free beer based on the urinalysis, and the investigative computer 200 may transmit the QR code 260 to the user's mobile computer 272 to allow the user 270 to redeem same. The user 270 may use the rewards manager 286 to pull up the QR code 260 (and to view and manage other rewards awarded by the rewards appraiser 216) on his mobile computer 272 for redemption.

The health manager 288 may, in embodiments, store and allow the user 270 to access the results of urinalysis conducted at any smart urinal 100. For example, the health manager 288 may store the results from the health screeners 210 of various urinals 100 used by the user 270. These results may be time and date stamped, and may afford the user 270 the opportunity to monitor his health on a regular basis. In some embodiments, particularly where such local storage of medical data of an individual violates applicable laws (e.g., HIPAA), the health manager 288 may be omitted and the urinalysis results may instead be stored securely and remotely (e.g., on the cloud, discussed further below).

In some embodiments, the smart urinal alert generator 224 may generate an alert and communicate same to the mobile computer 272. The alert manager 290 may allow the user 270 to customize the way in which alerts are communicated from the mobile computer 272 to the user 270. For instance, where the user 270 is a diabetic, the user 270 may configure the alert manager 290 such that the mobile computer 272 beeps (and/or vibrates) each time the urinalysis indicates the user's sugar levels are above some user-defined threshold. Alternately, where the user 270 knows that he has urinary tract infection, for example, he may configure the alert manager 290 such that alerts generated by the alert generator 224 regarding a urinary tract infection are automatically discarded for a given user-defined or other time period.

In embodiments, the urinalysis results of the user 270 may be encrypted and stored on secure network storage. For example, the urinalysis results of the user 270 may be encrypted and stored on the "cloud" 292. The investigative computer 200 may have a cloud API 293 which may allow the urinal 100 to securely communicate with the cloud 292. As can be seen, the cloud (or other secure network storage) 292 may include a plurality of records 300A-300N associated with the user 270. And the cloud storage may likewise include records of other users of the urinal 100.

FIG. 7 shows the example record 300A of the user 270 stored in the cloud 292. The record 300A may contain a plurality of fields 302. For example, in an embodiment, the record 300A may include a field 304 for the name of the user 270, a field 306 for the device identification number of the mobile computer 272 associated with the user 270, the urinalysis results 308 compiled by the health screener 210, the date and time 310 at which the urine with which the particular results 308 are associated was voided, the name, city, and geospatial coordinates 312 of the entity 240 within which the urinal 100 is located, rewards 314, the user's biometric sample 316, any alert 318 generated by the alert generator 224, any recommendation 320 generated by the recommendation generator 218, etc.

The user 270 may provide at least some of this information when he downloads and installs the mobile application 284 (e.g., the user 270 may provide his name 304 (John in this example) upon installation of the mobile application 284). The mobile application 284 may likewise retrieve the device identification number (e.g., an Android ID, a Google Advertising ID, a Universal Device ID, etc.) of the particular mobile device 272 associated with the user 270 upon installation, and may further require the user 270 to submit a biometric sample (fingerprint in this example) so that subsequent biometric samples provided by the user 270 at the urinal 100 may be compared against the initial sample. Some fields in the user record 300A (e.g., the health screener results 308) may be generated once the urinalysis is complete. When the user record 300A is completed, it may be securely stored in the cloud 292.

The FIG. 7 record 300A shows, for example, that a user 304 named John, having a device Id 306 of 123456, voided his urine at a urinal in Overland Park, Kans. on Nov. 1, 2016 at 2:00 pm. The record 300A also indicates that the user's health screener results 308 indicate high sugar levels, and that an alert 318 and a recommendation 320 about same was conveyed to the user 270. The record 300A further shows that the user 270 has two free beers in rewards at the entity 240. In some embodiments, for ease of record keeping and maintenance, in addition to a device ID 306 that is associated with each unique mobile computer 272, a unique numeric or alphanumeric identification number may be associated with each entity 240 and with each smart urinal 100. Further, in some embodiments, the user records (e.g., user record 300A) may contain only event specific information and the invariable information associated with the user (e.g., his name 304, device identification number 306, etc.) may be stored on the cloud 292 in a separate profile associated with the user 270.

In some embodiments, in generating an alert 318 and/or a recommendation 320, the alert generator 224 and the recommendation generator 218 of the investigative computer 200 may respectively take into account the user's historical records 300A-300N. For example, the alert generator 224 may not generate an alert 318 even where the urinalysis of the user 270 indicates that the user 270 has a sexually transmitted disease, where the user records further indicate that the user 270 has recently been alerted about same a plurality of times. In some embodiments, the alerts 318 communicated to the mobile device 272 may include "read-receipt" functionality so that the software 208 can check whether the alerts 318 are timely viewed by the user 270; if they are not, the alert generator 224 may resend same and may cause the mobile device to ring (and/or vibrate). The artisan will appreciate that the communications (e.g., alerts 318, recommendations 320, rewards 314, etc., may be communicated from the investigative computer 200 to the mobile device 272 in any suitable manner (e.g., over Bluetooth, via text, over e-mail, over voicemail, etc.).

Figure 8A:
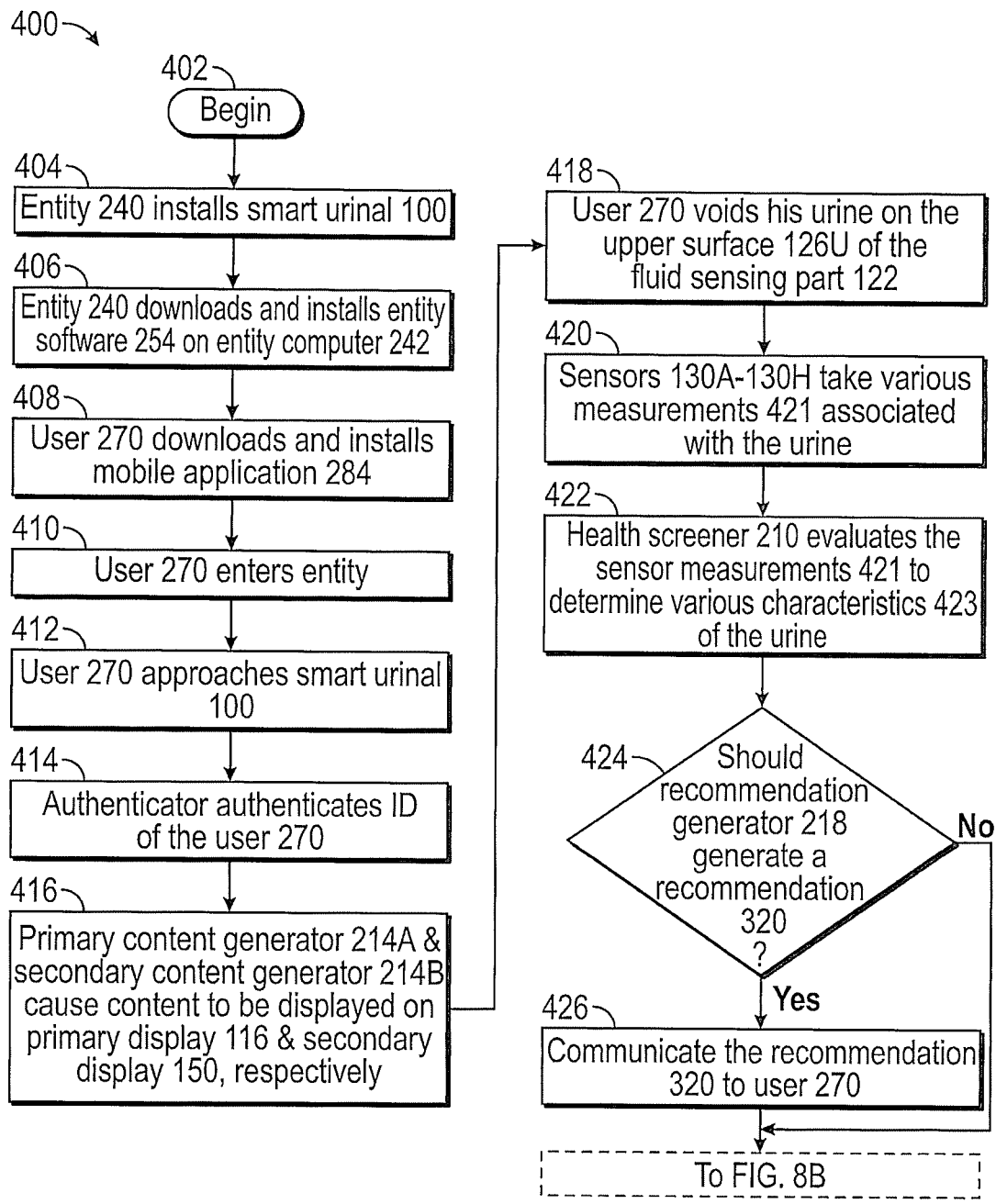
FIGS. 8A-8B show a flowchart illustrating an example method of using the smart urinal.
Figure 8B:
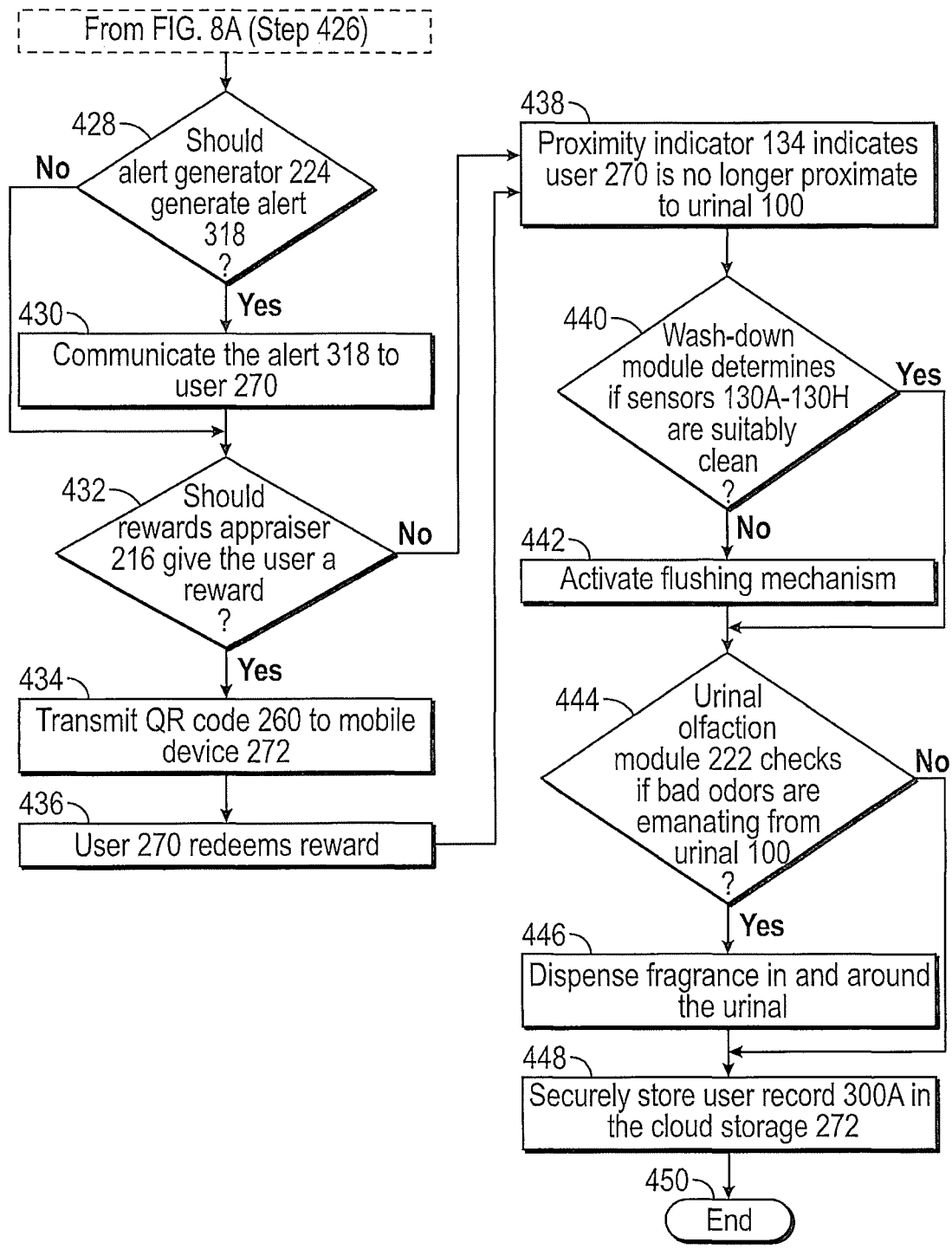

FIG. 8 shows an example method 400 of using the smart urinal 100, according to an embodiment. The method 400 may begin at step 402. At step 404, the entity 240, having the entity computer 242, may install one or more smart urinals 100 (e.g., in a restroom). Alternately, the entity 240 may convert its prior art urinal(s) to the smart urinal(s) (e.g., by installing the analysis portal 120 in the prior art urinals). While the entity 240 in this example is a bar (i.e., David's Bar, see FIG. 7), the artisan will understand that the entity 240 may be a gym, hospital, group home, private residence, or any other establishment or location where urinal(s) may be found. At step 406, the entity 240 may download and install the entity software 254 onto the entity computer 242. In embodiments, the entity 240 may also download and install the entity software 254 prior to installation of the smart urinal 100 at the entity 240.

At step 408, the user 270 may download and install on his mobile computer 272 the mobile application 284. In so doing, the user 270 may provide and/or the application 284 may otherwise ascertain certain identifying information, such as the name 304 of the user 270, the identification number 306 of the mobile device 272 associated with the user 270, the biometric sample 316 against which subsequent biometric samples provided by the user 270 are to be compared, etc. The artisan will understand that the user 270 may download and install the mobile application 284 on his mobile computer 272 before the particular entity 240 installs the smart urinal 100.

At step 410, the user 270 may enter the entity 240. At step 412, the user 270 may feel the urge to urinate, and may approach the urinal 100.

At step 414, when the user 270 is proximate the urinal 100, the investigative computer 200 of the urinal 100 may authenticate the user 270. For example, when the user 270 is within a few (e.g., 1-24) inches of the proximity detector 134, the authenticator 213 of the urinal 100 may use the network interface 204 to wirelessly communicate with the mobile computer 272 of the user 270. The authenticator 213 may retrieve the identification number 306 of the mobile device 272, and thereby determine that the mobile device 272 is associated with the user 270 (i.e., with John in this example). Alternately, in embodiments where the urinal 100 includes a biometric sensor 152 (see FIG. 1), the user 270 may provide his biometric sample (e.g., a fingerprint scan) at the urinal 100 and the authenticator 213 may authenticate the user 270 by ensuring that the biometric sample the user 270 provided during installation of the mobile application 284 matches the sample the user 270 now provided at the urinal 100.

At step 416, the primary content generator 214A and the secondary content generator 214B may cause primary display content 116C and secondary display content 154 to be displayed on the primary display 116 and the secondary display 150, respectively. As discussed above, the primary display content 116C and/or the secondary display content 154 may be personalized (and at least generalized content may be displayed on the primary display 116 and/or the secondary display 150 before the user is proximate the urinal 100). For instance, and as shown in FIG. 1, the primary content generator 214A may display the name 304 (i.e., John in this example) of the user 270 on the primary display 116, along with a message informing John that he can void his urine on the target and obtain a free drink (see FIG. 1). The secondary content generator 214B may, in this example, generate target indicia on the secondary display 150 to encourage the user 270 to void his urine directly onto the analysis portal 120 (and particularly, on the sensor 130D thereof).

At step 418, the user 270 may void his urine on the analysis portal 120, and more specifically, on the upper surface 126U of the sensing part 122. For example, the user 270 may void his urine directly on the fluid sensing region 128D. The urine may thus flow from the fluid sensing region 128D to the other fluid sensing regions 128A-C and 128D-H. At step 420, and as discussed above, the sensors 130A-130H may take various measurements 421 associated with the urine (e.g., sensor 130D may determine the pressure at which the urine is voided, sensor 130F may determine the sugar content of the urine, sensor 130G may determine the temperature of the urine, etc.). At step 422, the health screener 210 of the investigative computer software 208 may analyze these readings from the sensors 130A-130H to determine various characteristics 423 of the urine of the user (e.g., the drugs module 212A may evaluate the readings from the drug sensor 130A to determine if the user 270 has taken drugs, the sugars module 212F may evaluate the readings from the sugar sensor 130F to determine whether the user's urine contains normal or abnormal sugar levels, etc.).

At step 424, the recommendation generator 218 may determine whether the urinalysis indicates that a recommendation (e.g., recommendation 320, see FIG. 7) is to be generated for the user 270. If so, at step 426, the recommendation generator 218 may communicate the recommendation 320 to the user 270. For example, the recommendation generator 218 may transmit the recommendation 320 to the mobile device 272; alternately or in addition, particularly where the recommendation is not personal in nature, the recommendation generator 218 may cause the recommendation 320 to be displayed on the primary display 116 (or another display) at step 426. The memory 206 may include a database storing recommendations for a plurality of scenarios and further outline whether or not the recommendation is to be publically displayed (e.g., any recommendation suggesting the user 270 consult a physician may be considered personal and may be transmitted to the mobile device 272 but may not be displayed on the primary display 116). In embodiments, and as discussed above, when determining whether to generate a recommendation, the recommendation generator 218 may take into account the historical records of the user 270 stored on the cloud 292. If the recommendation generator 218 determines that no recommendation is to be generated, the method 400 may move from step 424 directly to step 428.

At step 428, the alert generator 224 may determine whether results of the urinalysis are cause for alarm such that an alert notification (e.g., alert notification 318, see FIG. 7) needs to be communicated to the user 270. If so, at step 430, the alert generator 224 may communicate an alert to the user 270. As discussed immediately above for the recommendation 320, the alert 318, if generated, may be communicated to the user 270 via his mobile device 272 and/or may be displayed on the primary display 116. In embodiments, when determining whether to generate an alert, the alert generator 224 may take into account the historical records of the user 270 stored on the cloud 292. If the alert generator 224 determines that no alert is to be generated, the method 400 may move from step 428 directly to step 432.

At step 432, the rewards appraiser 216 may determine if the urinalysis indicates that the user 270 is entitled to a reward. If so, at step 434, the rewards appraiser 216 may cause the QR code 260 (FIG. 6) associated with the reward to be wirelessly transmitted to the mobile computer 272. In some embodiments, one or more of the tests conducted during the urinalysis may be relatively time-consuming (e.g., may take a few minutes or even an hour or more to complete); in these embodiments, the rewards appraiser 216 may evaluate whether a reward is to be given to the user 270 before it completes the entire urinalysis, and the completed urinalysis results may be stored in the cloud storage 292 as discussed below. At step 436, or at some point thereafter, the entity 240 may use the scanner 246 of the entity computer 242 to scan the QR code 260 and allow the user 270 to redeem the reward. The method 400 may move to step 438. Alternately, if the rewards appraiser 216 determines that the user 270 is not entitled to an award at step 432, the method 400 may move from step 432 directly to step 438.

At step 438, the proximity detector 134 (FIG. 1) may indicate that the user 270 has finished urinating and is no longer proximate the urinal 100. At step 440, the wash-down module 220 may take test readings to determine whether the sensors 130A-130H are suitably clean. If not, the wash-down module 220 may activate the flushing mechanism at step 442, and continue to do so until the test readings from the sensors 130A-130H indicate that they are ready for use. Alternately, if the wash-down module 220 determines at step 440 that the sensors 130A-130H are suitably clean, the method 400 may move from step 440 to step 444. As discussed above, the wash-down module 220 may, in embodiments, cause sanitation agent stored in the vessel 156 to be dispensed into the urinal 100 during the wash-down mode. In embodiments where the smart urinal 100 automatically flushes when the proximity detector 134 indicates that the user 270 is no longer proximate the urinal 100, the wash-down module 220 may take test readings after the initial automatic flushing is effectuated.

At step 444, the urinal olfaction module 222, using an olfactory sensor, may ascertain whether bad odors are permeating from the urinal 100. If so, at step 446, the urinal olfaction module 222 may dispense a fragrance in and/or around the urinal 100. The fragrance may be stored in the vessel 156 and may be chosen so that it does not materially impact the readings from the sensors 130A-130H. Alternately, if the urinal olfaction module 222 determines that no bad odors are permeating from the urinal 100, the method may move from step 444 to step 448.

At step 448, the fields (e.g., the fields 302 in the user record 300A) may be filled out by the investigative computer 200, and the user record 300A may be securely stored on the cloud storage 292. The user record 300A stored on the cloud 292 may be encrypted, password-protected, and/or otherwise secured such that it is only accessible to authorized personnel and computing devices. In embodiments, the user record 300A, or portions thereof, may also be transmitted to the mobile computing device 272. The method 400 may then end at step 450.

In certain applications, it may be desirable to store a portion of a urine sample being tested by the portal 120 for subsequent analysis and/or verification. For example, as illustrated by a recent scandal at the Olympics in Russia, and particularly where a urine test is conducted as a precondition, e.g., to employment, to a sports tournament, etc., the urinalysis is susceptible to being doctored. In some embodiments, therefore, a portion of the urine voided by a user may be tested by the analysis portal 120, and the remainder (or at least a portion thereof) may be stored (e.g., in a watertight vial) that can be retrieved by authorized personnel. The sample of the urine in the vial may therefore be retested (e.g., in a lab) if desired. The vial may be stamped with the user's name and other pertinent information (e.g., date, time, etc.). In embodiments, the analysis portal 120 may be configured to push a predetermined volume of urine directly into a vial for storage, and a lockable housing may be associated with the urinal body for storage of the vials.

The analysis portal 120, the primary display 116, and the other components may be powered by standard AC power (e.g., 110V), by batteries, and/or other means (e.g., inductively).

In some embodiments, more than one analysis portal 120 may be associated with the urinal. For example, one analysis portal 120 may be situated within the urinal 100 as shown in FIG. 1, and one or more analysis portal(s) 120 may be situated on a back side of the urinal 100 or elsewhere; in these embodiments, the urinal 100 may include a moving mechanism (e.g., a conveyer belt or other system) which may rotate the analysis portals 120 for use (e.g., each analysis portal 120 may be rotated out after it is used by ten, twenty, or some other predefined number of users).

Users may be wary of using urinals that have a camera associated therewith. The smart urinal 100, in embodiments, may be devoid of any cameras, and the appearance of the urinal 100 may be inviting and non-threatening. That is, in embodiments, users (e.g., the user 270) may readily appreciate that the urinal 100 is a relatively non-invasive novelty urinal that also includes additional functionality. In embodiments, the mobile application 284 may include a competition mode, and a group of users (e.g., friends at a bar) may compete with each other to obtain rewards based on their respective urinalysis.

In the prior art, employers, schools, and others may, from time to time, require that a user travel to a urinalysis lab to have his urine tested (e.g., for drugs). These tests, as noted above, may be inconvenient, and their collective cost, particularly over longer time spans (e.g., five years, ten years), may be exorbitant. Entities may therefore purchase and install the smart urinals 100 and thereby obviate the need to send users to labs for urinalysis; for example, a sports team may install the smart urinals 100 at its gym and use same for decades to ensure that no team member is drunk or taking drugs. Further, advertisements (and other programming) that may be displayed via the smart urinal 100 (e.g., on the primary display 116) may allow an establishment to readily recoup the costs associated with purchasing and installing these urinals 100.

In some embodiments, the user 270 may be charged a fee to download and use the mobile application 272 to interact with the urinal 100. Alternately or in addition, the user 270 may be charged a nominal fee each time his urine is evaluated by the smart urinal 100. Some establishments may allow users to use the smart urinal 100 free of charge to garner customer goodwill. While FIG. 5 shows a solitary investigative computer 200 in communication with the entity computer 242, the artisan will readily appreciate that in embodiments, a plurality of smart urinal investigative computers 200 may be in data communication with the entity computer 242. Further, in embodiments, the investigative computers 200 of a plurality of smart urinals 100 may be networked together such that an owner or operator may make global changes to the functionality of the urinals 100

(e.g., an owner or operator may modify the content being displayed on the various urinals 100 simultaneously).

As noted above, structural changes may be made to conventional prior art urinals to convert same to smart urinals (e.g., channels may be etched in the urinal body 102 to locate sensors therein, a portion of a prior art urinal body 102 may be cutout to allow for the situation of the analysis portal 120 therein, etc.). Such retrofitting, referred to herein as permanent retrofitting, however, may not be required in all embodiments. Rather, in some embodiments, a prior art urinal may be temporarily converted to a smart urinal using a personal retrofitting device. Specifically, and as discussed above, the analysis portal 120 may, in embodiments, have a fluid accepting portion 120 that is configured to contact the urine of a user directly to functionally interact therewith. In other embodiments, however, the analysis portal 120 may be configured to functionally interact with fluids (e.g., the urine of a user) remotely. For instance, in embodiments, at least some of the functionality of the analysis portal 120 may be encompassed within a mobile device (e.g., a smart phone, a smart watch, smart glasses, etc., of a user) having non-contact sensors (e.g., photoelectric sensors, inductive sensors, capacitive sensors, ultrasonic sensors, etc.) that can determine at least one characteristic (e.g., flow, color, etc.) of the user's urine without directly contacting the urine. In these embodiments, the user (e.g., the user 270) may walk up to the urinal with the analysis portal on his person (e.g., in his hand, in his pocket or a bag, etc.), and the urinal may detect the analysis portal and convert temporarily into a smart urinal. That is, the non-contact sensors of the analysis portal may evaluate the urine when the user is urinating at the urinal without physically contacting same. As with other embodiments discussed above, the analysis portal may have a display (e.g., where the analysis portal is a smart phone, its display may constitute the primary display and/or the secondary display) and the portal may communicate (e.g., wirelessly) with the user 270 and others based on the urinalysis. When the user 270 walks away from the urinal, a communication session between the analysis portal and the urinal may be terminated and the urinal may act as a traditional urinal. In these embodiments, thus, any urinal may be temporarily converted to a smart urinal via the personal retrofitting device/analysis portal.

In some embodiments, the primary display 116 and/or the secondary display 150 may not be conventional displays (e.g., monitors, televisions, smart phone or other screens), but may simply be areas of the urinal body 102 configured to display content. For example, in embodiments, the primary display 116 may be an area of the urinal body 102 configured to display content projected onto zone C (or another zone) of the urinal 100 by the analysis portal (e.g., a mobile device such as a smart phone). Thus, the term display, as used herein, encompasses traditional displays and any and all other modes that may be used to display content. For instance, in an embodiment, the user's mobile device may encompass some or all of the functionality of the analysis portal, and may cause content to be displayed (e.g., projected) on the urinal body 102 when the user is at the urinal 100.

In some embodiments, the mobile computer 272 may be a mobile device that is worn by the user 272 (e.g., wristbands, smart glasses, etc.). For instance, in embodiments, the mobile computer 272 may be a wristband worn by the user 270 which changes colors based on the urinalysis results (e.g., the wristband may turn from green to red where the blood alcohol of the user 270 is above the legal driving limit, and change back from red to green after a given time period taking into account the user's body weight and blood alcohol level to indicate that the user 270 is now sober). Such may, for example, allow law enforcement to readily determine that a particular user 270 on the road is intoxicated.

As discussed, in some embodiments, structural changes may be made to prior art urinals so that the analysis portal, such as the analysis portal 120, may be disposed inside the urinal body interior part 102I. For example, the analysis portal 120 may be situated within the cutout 102C in the back portion 104 of the urinal body 102 (see FIG. 1) so that a user may void his urine directly on the fluid sensing region 128D (or another fluid sending region 128) of the analysis portal 120. In other embodiments, a mobile device configured to be carried by the user on his person may constitute the analysis portal. For instance, a smart phone having non-contact sensors may include at least some of the functionality of the analysis portal 120, and may functionally interact with the user's urine during a communication session that extends while the user is urinating at a urinal (e.g., at the urinal 100 or another urinal).

Figure 9:
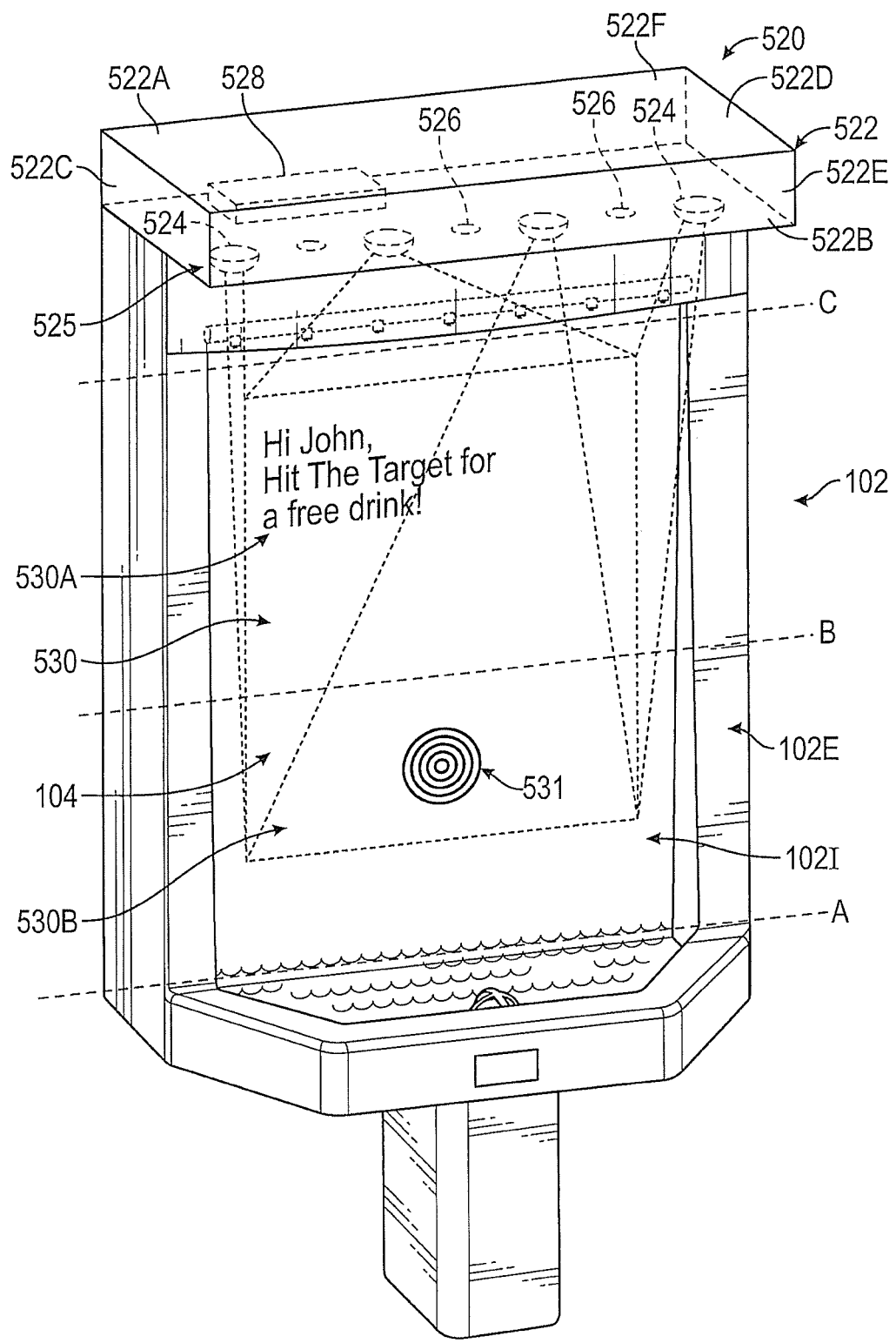
FIG. 9 shows a perspective view of an alternate embodiment of the analysis portal of FIG. 2 in use with a urinal.

Focus is directed now to FIG. 9, which shows an alternate embodiment 520 of the analysis portal 120. The analysis portal 520 may be similar to the analysis portal 120, except as specifically noted and/or shown, or as would be inherent. Further, those skilled in the art will appreciate that the analysis portal 120 (and thus the analysis portal 520) may be modified in various ways, such as through incorporating all or part of any of the various described embodiments, for example. For uniformity and brevity, corresponding reference numbers may be used to indicate corresponding parts, though with any noted deviations.

Three primary differences between the analysis portal 120 and the analysis portal 520 may be as follows: (1) the analysis portal 120 may be situated within the urinal body interior 102I whereas the analysis portal 520 may be situated outside the urinal body 102; (2) one or more of the sensors 130 of the analysis portal 120 may come into contact with a user's urine, whereas the analysis portal 520 may include only non-contact sensors that functionally interact with a user's urine without the urine coming into direct contact with the sensors; and (3) the primary display 116 and the secondary display 150, on which content is respectively displayed by the primary content generator 214A and the secondary content generator 214B of the analysis portal 120/investigative computer 200, may be physical displays located within the urinal body interior 102I, whereas the content generator associated with the analysis portal 520 may cause content to be projected onto the urinal body interior 102I. In some embodiments, a urinal (e.g., the urinal 100 or another urinal) may include two or more analysis portals; for example, an analysis portal (e.g., the analysis portal 120) may be situated within the urinal body interior 102I and another analysis portal (e.g., the analysis portal 520) may be situated outside (e.g., atop) the urinal body 102. The analysis portal 520 may also be referred to herein as the urinal accessory 520 or the urinal retrofitting device 520.

The analysis portal 520 may include a housing 522 (FIG. 9), which may be made of metal, plastic, and/or other desirable materials. The housing 522 may be disposed proximate the urinal body 102. For example, the urinal body exterior 102E may include a top wall 131 (see FIG. 1), and the analysis portal housing 522 may be disposed upwardly adjacent the top wall 131. In embodiments, the housing 522 may be generally rectangular and include: a top wall 522A, and a bottom wall 522B opposing the top wall 522A; a first sidewall 522C, and a second sidewall 522D opposing the first sidewall 522C; and, a front wall 522E, and a rear wall 522F opposing the front wall 522E. The sidewalls 522C and 522D of the housing 522 may protrude from the rear wall 522F towards the user using the urinal such that the housing bottom wall 522B extends past the top wall 131 of the urinal body exterior 102E. In some embodiments, the bottom wall 522B may be adjacent and in contact with the top wall 131, and in other embodiments, a gap (of e.g., 1 foot, 2 feet, etc.) may be provided between the urinal top wall 131 and the housing bottom wall 522B. The housing 522 therefore may, but need not, rest on the top wall 131 of the urinal body exterior 102E. Where the urinal body 102 is proximate an entity wall (e.g., where the recessed back portion 104 is situated proximate and in front of a wall of a restroom within which the urinal is situated), the analysis portal housing 522 may be mounted or otherwise secured (using e.g., nuts and bolts, adhesive, fastening strips, or other means) to the entity wall such that the housing bottom wall 522B is atop the top wall 131 of the urinal body 102 and extends past the top wall 131 towards the user. Alternately or in addition, the housing 522 may in embodiments be permanently or removably secured to the urinal body 102 itself (using e.g., straps, adhesive, fasteners, or other means) such that the housing bottom wall 522B is atop the top wall 131 of the urinal body exterior 102E and extends past the top wall 131. The portion of the housing 522 that protrudes towards the user past the urinal body top wall 131 may be referred to herein as the overhanging portion 525 of the housing 522.

In an embodiment, the housing 522 of the analysis portal 520 may house at least one or more content projectors 524, one or more sensors 526, and additional electronics 528, each of which are described in more detail below. The electronics 528 may include, among other things, a processor having memory and software to control the operation of the content projectors 524 and the sensors 526. In embodiments, the electronics 528 may also include one or more of a speaker, a networking device (e.g., a Bluetooth, Wi-Fi, or other networking device), a global positioning system, LED or other novelty lights, etc.

The content projectors 524, the sensors 526, and/or the electronics 528 may, in embodiments, be powered using a conventional 110V/220V outlet; for example, the rear wall 522F may include one or more apertures to allow for these components to be powered via wires that extend through the aperture and couple the projectors 524, the sensors 526, and/or the electronics 528 to the outlet. In some embodiments, one or more of the content projectors 524, the sensors 526, and/or the electronics 528 may be powered by portable power generation sources (e.g., batteries). In other embodiments still, the projectors 524, the sensors 526, and/or the electronics 528 may be powered wirelessly (e.g., inductively). The artisan will appreciate that the various components of the analysis portal 520 need not be powered the same way.

The content projectors 524 may be LCD projectors, laser projectors, 3D projectors, 4K projectors, Pico projectors, or any other video or multimedia projectors. The housing 522 may at least partially encapsulate one or more such projectors 524. At least a part of the content projectors 524 may be situated in the overhanging portion 525 of the housing 522. For example, the lenses of the content projectors 524 may be mounted within openings in the bottom wall 522B of the overhanging portion 525 of the housing 522 so that the content projectors 524 project content for user consumption into the urinal body interior 102I (e.g., project content onto the recessed back portion 104). User consumable content (e.g., at least part of the content projected by the content projectors 524), as used herein, means content that includes a component in the visible electromagnetic spectrum.

In some embodiments, the housing bottom wall 522B may be angled with respect to the horizontal (e.g., the housing bottom wall 522B may make a 30 degree angle, a 45 degree angle, or at another desirable angle with the horizontal) so that the content projectors 524 project content onto the recessed back portion 104 (as opposed to projecting content straight down on the floor or only on the projection portion (see FIG. 1) of the urinal body 102). In some embodiments, the housing bottom wall 522B may be parallel to the horizontal but the content projectors 524 may be situated within the housing bottom wall 522B openings at an angle such that the content is projected onto the recessed back portion 104. The artisan will appreciate that any number and type of content projectors 524 may be employed in the analysis portal 520 so long as the content projectors 524 cohesively project content suitable for viewer consumption onto the urinal body interior 102I. Configuration of the projectors 524 (e.g., of the projection angle, zoom, etc.) for this particular application is a matter of routine for the skilled artisan. It will be appreciated that the dimensions (e.g., height, width, font size, etc.) of the content projected by the projectors 524 may be chosen to be commensurate with the dimensions of the urinal body onto which the content is being projected (for instance, the projected content for a small urinal may be 1 foot wide and 2 feet tall, whereas the projected content for a larger urinal may be 3 feet wide and 4 feet tall). The overall shape of the projected content may be rectangular, circular, triangular, etc., and may, in embodiments, correspond generally to the shape of the urinal wall onto which the content is being projected.

The content projected by the content projectors 524 (herein, projected content 530) may include video, multimedia, interactive, static or dynamic, or any other content, such as the primary display content 116C and/or the secondary display content 154 discussed above with respect to FIG. 1. In an embodiment, the projected content 530 may include an upper portion 530A and a lower portion 530B that is displayed beneath the upper portion 530A. The content lower portion 530B may include content that is configured to be responsive (specifically, content which appears to be responsive) to the urine of a user. For example, the urine responsive content may include target indicia 531, which, as discussed herein, may be configured to respond to the voiding of a user's urine thereon (e.g., the target indicia 531 may change colors as the user voids his urine on same). Alternately or in addition, the urine responsive content may comprise bowling pins projected onto the urinal body interior 102I that appear to fall as the user voids his urine on the bowling pins. Or, for example, the urine responsive content may include polls and the user may select the option he prefers by urinating on same. The urine responsive content, where employed, may be projected on those portions of the urinal body interior 102I that can be accessed by a user via the user's urine (e.g., on the middle zone B, the lower zone A, and/or the lower part of the upper zone C of the urinal back portion 104). The sensors 526 may be used to determine that the user is voiding his urine on a particular portion of the projected content 530 (e.g., the user is urinating on the urine responsive content).

In embodiments, the non-contact sensors 526 and the associated electronics 528 may be employed to determine one or more characteristics (e.g., position, color, temperature, presence, etc.) of the urine voided by a user within the urinal body interior 102I. In some embodiments, one or more of the sensors 526 may be situated in the overhanging portion 525 of the housing 522. Openings may be provided in the overhanging portion 525, e.g., in the bottom wall 522B, to allow the sensors 526 to functionally interact with the user's urine. One or more of the sensors 526 may be configured to scan downward at an angle (akin to the projectors 524 which project content downward at an angle), i.e., the sensors 526 may be directed towards those portions of the urinal body interior 102I that are likely to receive urine voided by a user. The determination of certain characteristics of the voided urine may be made before the urine contacts the urinal body interior 102I, and other characteristics of the urine may be determined after the urine contacts the urinal body interior 102I.

The sensors 526 may include, for example, one or more spectroscopic sensors having a light source (e.g., a near-infrared light source, a laser array, or other source for emitting energy within or outside the visible spectrum) associated therewith. The light sources associated with the spectroscopic sensors 526 may, in embodiments, allow for positional mapping of the portion of the urinal body interior 102I configured to receive urine voided by a user (e.g., the portion of the urinal back portion 104 onto which urine responsive content 530B is being projected). For example, the light sources may divide the urinal body interior 102I into sectors, which may, in embodiments, be non-overlapping. Voiding of the urine stream into the urinal body interior 102I (e.g., on a particular sector) may affect the light being reflected back to the sensor 526, and these reflections may be evaluated by the associated electronics 528 (e.g., software associated with a processor thereof as discussed below) to determine the location of the voided urine stream. In embodiments where the projected content 530 includes urine responsive content 530B, the content 530B being displayed may be modified in response to the voiding of the urine thereon. For example, where the sensors 526 and associated electronics 528 determine that the user is voiding his urine stream on the bull's eye of the target indicia 531 (i.e., where the positional mapping/reflected light characteristics indicate that the urine stream is being voided at the portion of the urinal interior 102I where the bull's eye of the target indicia 531 is currently being projected), the color of the target indicia may change from one color to another. Alternately, an audible signal (e.g., a clapping or other sound) may be employed to apprise the user that he has successfully hit the bull's eye of the target indicia 531. As discussed above for analysis portal 120 and in more detail below, in embodiments, the electronics 528 may in response to voiding of the user's urine determine that the user is entitled to a reward. In some embodiments, the electronics 528, via the sensors 526, may evaluate the reflections caused by the voiding of a user's urine into the urinal body interior 102I to quantify splatter, and correlate the splatter information to determine the intensity of the user's urine stream.

In embodiments, the sensors 526 may include non-contact infrared sensors (e.g., one or more arrays of passive infrared sensors) or other non-contact temperature sensors. The infrared sensors may be employed to determine the temperature of the urine stream. As discussed herein, where the temperature sensors indicate that the user's urine is unduly hot or cold, the electronics 528, e.g., software associated therewith as discussed below, may cause an alert to be displayed (e.g., projected on the urinal body 102) and/or cause the alert to be transmitted to the user via his mobile device.

In embodiments, the sensors 526 of the analysis portal 520 may include non-contact sensors configured for determining the color of the user's urine (e.g., color sensors developed by TI Instruments, MAZeT's color sensors, or other non-contact color sensors). The artisan appreciates that the color of a user's urine provides valuable insight into the user's health and overall well-being. For example, red hue of a user's urine may indicate that the user has kidney disease or a urinary tract infection, dark brown hue of a user's urine may indicate that the user is dehydrated, and so on. As discussed herein, where the color of the user's urine is cause for alarm, the analysis portal 520 may cause an alert to be generated and/or transmitted to the user's mobile device. In some embodiments, as discussed above for the analysis portal 120, a recommendation (e.g., a recommendation recommending that the user hydrate) may also be communicated to the user.

The sensors 526 may, in embodiments, include audible sensors. The audible sensors may, for example, be configured to discriminate between the various sounds originating within the restroom in which the analysis portal 520 is located (e.g., the electronics 528 may via the audible sensors distinguish between a user voiding his urine into the urinal body 102 and flushing the urinal). In some embodiments, particularly where the urinal is devoid of a proximity sensor, the audible sensors may be used to determine that the urinal is in use. In some embodiments, however, the analysis portal 520 may alternately or additionally include a proximity sensor (e.g., an infrared detector). While not required, in some embodiments, content 530 may be projected by the content projectors 524 onto the urinal body interior 102I only when the urinal is in use. In other embodiments, one type of content 530 may be projected onto the urinal body interior 102I while the urinal is not in use and another type of content 530 may be projected onto the urinal body interior 102I based upon a determination that the urinal is in use. For example, when the urinal is not in use, content 530 projected onto the urinal body interior 102I may include general content (as discussed above for the analysis portal 120), whereas personalized content (discussed above) may be projected when the urinal associated with the analysis portal 520 is in use. In some embodiments, content 530 may be projected onto the urinal body interior 102I once the identity of the user proximate the analysis portal 520 is confirmed (e.g., via a communication between an authenticator of the analysis portal 520 and a mobile device of the user, as discussed below).

While not required, the sensors 526 may in embodiments include visual sensors (e.g., CCD sensors, CMOS sensors, and/or other cameras). As noted above, however, users may be wary of using urinals that have a camera associated therewith. Therefore, where visual sensors are employed, care may be taken to ensure that any images captured and evaluated (e.g., for health screening purposes) are deleted after the evaluation. Alternately and/or in addition, the visual sensors, where employed, may be configured to read only the wavelengths of light in the sensor array, and may be incapable of rendering images for human consumption.

Figure 10:
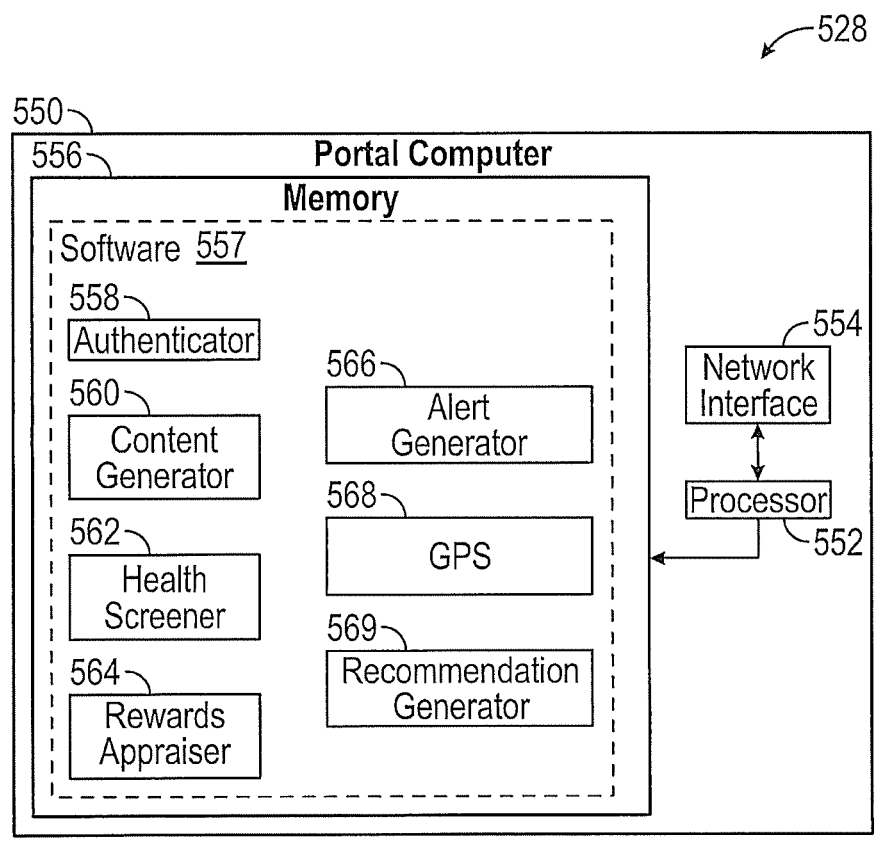
FIG. 10 schematically illustrates electronics associated with the analysis portal of FIG. 9, according to an example embodiment.

FIG. 10 schematically represents the electronics 528 associated with the projectors 524 and the sensors 526, according to an embodiment. The artisan will appreciate that the electronics 528 illustrated in FIG. 10 are exemplary only and are not meant to be independently limiting.

The electronics 528 may include a computer 550 of the analysis portal 520. The portal computer 550, like the investigative computer 200 discussed above for the analysis portal 120, may include a processor 552, and a network interface 554 and memory 556 communicatively coupled thereto. Processor 552 represents one or more digital processors, and in embodiments, may be configured through particularly configured hardware, such as an application specific integrated circuit (ASIC), field-programmable gate array (FPGA), etc., and/or through execution of software to perform functions in accordance with the disclosure herein. Network interface 554 may be implemented as one or both of a wired network interface and a wireless network (e.g., Wi-Fi, Internet, Bluetooth, etc.) interface, as is known in the art. Memory 556 represents one or more of volatile memory (e.g., RAM) and non-volatile memory (e.g., ROM, FLASH, magnetic media, optical media, etc.). Although shown within the portal computer 550, memory 556 may be, at least in part, implemented as network storage that is external to the analysis portal 520 and accessed via network interface 554. For example, memory 556 may at least in part reside on the "cloud" and be remotely accessible via computing devices of authorized personnel.

Software 557 may be stored in a transitory or non-transitory portion of the memory 556. Software 557 includes machine readable instructions that are executed by processor 552 to allow the analysis portal 520 to function as described herein. In the illustrated embodiment, the software 557 contains an authenticator 558, a content generator 560, a health screener 562, a rewards appraiser 564, an alert generator 566, a global positioning system 568, and a recommendation generator 569, each of which are described in more detail below. While certain software modules are identified herein, in embodiments, other modules may also be provided in the software 557; similarly, one or more of the illustrated modules may, in embodiments, be omitted from the software 557.

The functionality of the authenticator 558 may be similar to that of the authenticator 213 (FIG. 5) discussed above. Specifically, in embodiments, the authenticator 558, via the network interface 554, may communicate with a mobile computer (e.g., smart phone 272) of a user to verify the identity of the user. For example, in some embodiments, a user may download a mobile application to allow him to interact with the analysis portal 520. During the installation process, a unique number associated with the user's mobile computer (e.g., an Android ID, a Google Advertising ID, etc.) may be retrieved and stored (e.g., in the memory 556 or another memory). When the user walks up to the urinal, the authenticator 558 may use the network interface 554 to interact with the user's mobile computer (e.g., over a Bluetooth or other network) to determine the device ID of the user's mobile computer. The authenticator 558 may thereafter correlate the device ID obtained when the user is proximate the analysis portal 520 with the device ID retrieved during the mobile application installation, and thereby, identify and authenticate the user. Alternately or in addition, in some embodiments, the analysis portal 520 may include a biometric sensor (e.g., a forward facing retinal scanner or other biometric sensor housed in the housing 522). In these embodiments, the authenticator 558 may identify the user by comparing the biometric sample he provides when he is proximate the analysis portal 520 with a biometric sample provided by the user previously (e.g., upon the mobile application installation).

The content generator 560 may cause the content projectors 524 to project content 530 onto the back portion 104 (or the back portion 104 and the projecting portion 106). As noted above, the projected content 530 may include, for example, general content (e.g., TV shows, non-targeted advertisements, news, etc.), personalized content (e.g., targeted advertisements, an individualized message containing the user's name or other identifying information as shown in FIG. 9, etc.), urine responsive content (e.g., target indicia 531 that changes colors when a user urinates thereon, bowling pins that fall down upon the voiding of a user's urine on same, etc.), and/or any other user consumable video or multimedia content.

The health screener 562 may be configured to evaluate the readings obtained from the sensors 526 from a health and wellness standpoint. In embodiments, the memory 556 may include average (i.e., normal) values for the particular characteristic being evaluated. For instance, the memory 556 may include a temperature range within which a user's urine's temperature should fall; where the health screener 562 determines that the temperature of the user's urine as determined by the temperature sensors is outside the normal range, the health screener 562 may communicate with the alert generator 556 (discussed further below) to cause it to communicate an alarm condition to the user (e.g., over his mobile device, or by projecting the alarm condition onto the urinal back portion 104). Similarly, where the health screener 562 determines via evaluation of the urine's color that the user is dehydrated (or determines that another characteristic of the user's urine is outside normal parameters), it may cause the alert generator 566 to convey an alert to the user. In some embodiments, as discussed above for the analysis portal 120, historical records of the user may be evaluated before an alert or recommendation is communicated to the user (e.g., if a user's historical records indicate that the user has previously been alerted about the hue of his urine on multiple occasions, the analysis portal 520 may forego communicating the alert to the user even where the health screener 562 determines that the hue of the user's urine is cause for alarm).

In embodiments, the rewards appraiser 564 may cause the user to be given a reward in response to the user voiding his urine into the urinal associated with the analysis portal 520. For example, in embodiments, where the user voids his urine on the target indicia 531 (as determined using the sensors 526), the rewards appraiser 564 may award the user a reward. The reward may be communicated to the user over his mobile device (e.g., a barcode associated with the reward may be communicated by the analysis portal 520 to the user's smart phone). As with the analysis portal 120 and its reward appraiser 216, the reward awarded by the reward appraiser 564 may be associated with the particular establishment within which the analysis portal 520 is located. For instance, the reward awarded by the rewards appraiser 564 of an analysis portal 520 situated in a bar may be a free beer, and a reward awarded by the rewards appraiser 564 of an analysis portal 520 situated in a coffee shop may be free (or discounted) coffee. Like the analysis portal 120, the analysis portal 520 may, in embodiments, allow the user to play games of skill and/or games of chance while he is voiding his urine at the urinal associated with the analysis portal 520. For example, the user may, in embodiments, use his urine stream to play virtual slots or blackjack; in these embodiments, monies (or other rewards) may be transmitted to the user or collected from the user via the user's mobile device (using, e.g., a third party digital wallet service).

The alert generator 566 and the recommendation generator 569, as discussed above, may be in communication with the health screener 562, and may communicate alerts and/or recommendations to the user in one or more of any number of ways. For example, the alert or recommendation may be projected onto the urinal back surface 104, communicated to the user and/or third parties via their respective computing devices, communicated as an audible alarm, etc. In embodiments, each of an alert and a recommendation may be respectively communicated to a user by the alert generator 566 and the recommendation generator 569. For example, where the color of the user's urine indicates that the user is dehydrated, the alert generator 566 may project an alert on the urinal back portion 104 communicating same to the user, and the recommendation generator 569 may send an SMS, e-mail, or other message to the user's mobile device recommending that the user enjoy a particularly hydrating drink being offered at the bar in which the analysis portal 520 is located.

The analysis portal 520 may, in embodiments, be configured to be easily disassociated from particular urinal (e.g., the analysis portal 520 may, in embodiments, be easily moved from one urinal to another, or to a machine shop for maintenance). The global positioning system 568 may be configured to indicate the current location of the analysis portal 520 (specifically, of the portal computer 550 thereof). The software 557 may use data from the global positioning system 568 to adaptively modify the operation of the analysis portal 520 as desired (e.g., where the analysis portal 520 is moved from one urinal in a bar to another urinal in a gym, the reward awarded by the rewards appraiser 564 may automatically change from a free beer to a free flex dollar). In some embodiments, any readings associated with a user and stored (e.g., in the memory 556) may be stamped with the global positioning data (in addition to, for example, the date and time associated with the reading).

The top mounted analysis portal (e.g., the analysis portal 520) may thus allow for any prior art urinal to be easily retrofitted (i.e., converted into a smart urinal) without the need to make any structural change to the body of the urinal.

Figure 11:
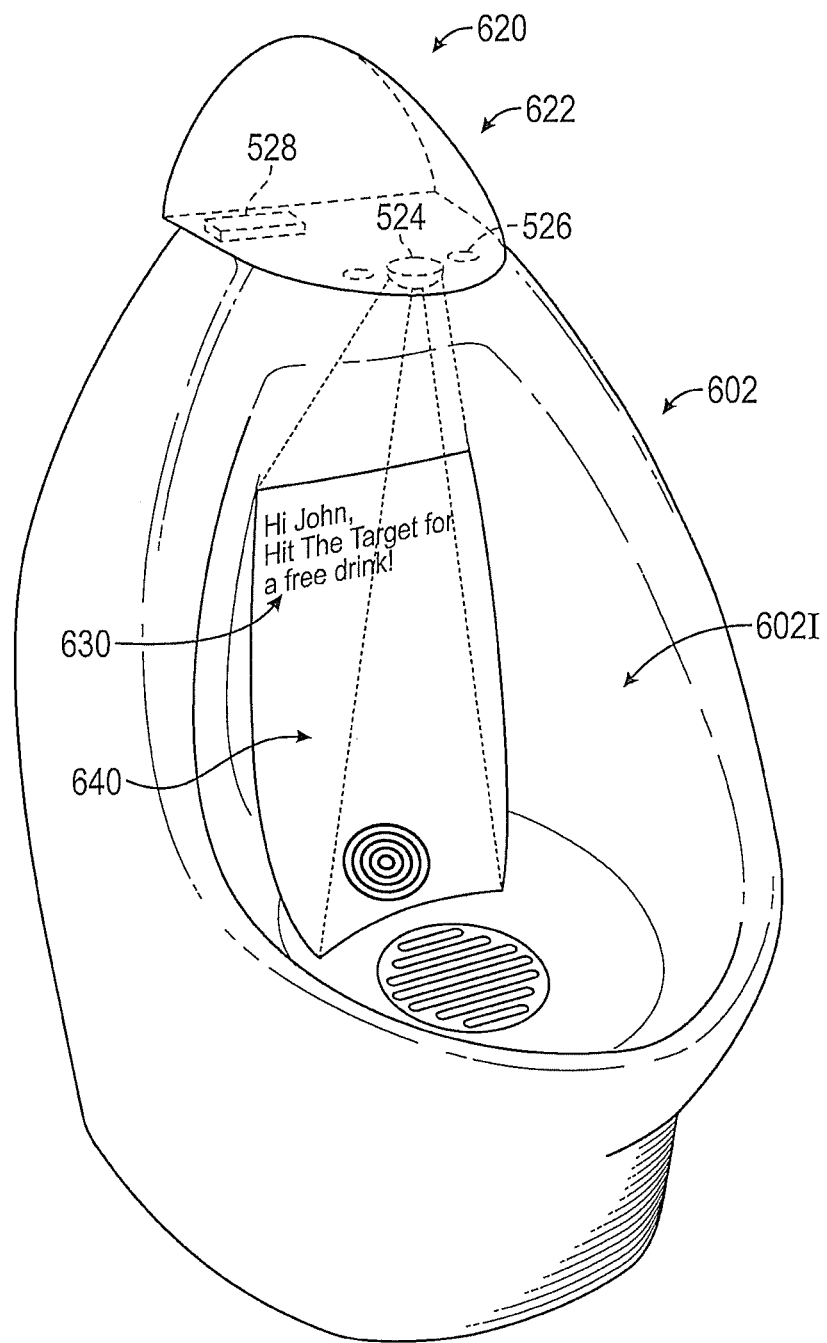
FIG. 11 shows a perspective view of another embodiment of the analysis portal of FIG. 2 in use with a projector screen disposed within a urinal.

Attention is directed now to FIG. 11, which shows an alternate embodiment 620 of the analysis portal 520. The analysis portal 620 may be similar to the analysis portal 520, except as specifically noted and/or shown, or as would be inherent. Further, those skilled in the art will appreciate that the analysis portal 520 (and thus the analysis portal 620) may be modified in various ways, such as through incorporating all or part of any of the various described embodiments, for example. For uniformity and brevity, corresponding reference numbers may be used to indicate corresponding parts, though with any noted deviations.

A primary difference between the analysis portal 520 and the analysis portal 620 may be the shape of their respective housings 522 and 622. As can be seen, the analysis portal 520 is associated with a urinal having a body 102 that is different from a body 602 of the urinal with which the analysis portal 620 is associated. The artisan will thus appreciate that the analysis portal housing need not be rectangular, but may take on any symmetrical or non-symmetrical shape so long as the housing 622 extends past the top wall of the urinal body 602 to allow: (a) the content projector(s) 524 to project content within the body interior 6021; and/or (b) for functional interaction between the sensors 526 and the urine voided by a user in the urinal.

The artisan understands that urinal bodies (e.g., the urinal body 102, the urinal body 602, etc.) may have different shapes and may comprise different materials (e.g., stainless steel, plastic, ceramics, etc.). The interior surfaces of certain urinals may have a shape that is not conducive to displaying content projected thereon. Further, some urinal bodies (e.g., the urinal body 602) may comprise materials that are not suitable for displaying projected content. In such cases, the analysis portal (e.g., the analysis portal 620) may have associated therewith a display sheet or panel 640. The display sheet 640 may be unpowered and comprise polyethylene, polycarbonate, Teflon coated plastic, coated metal, and/or other suitable material(s) that allow the display sheet 640 to display content projected thereon. In embodiments, the display sheet 640 may be non-planar (e.g., may be curved to correspond to a curved back wall of the urinal with which the analysis portal 620 is associated). The display sheet 640 may be secured (using waterproof adhesive, waterproof fasteners, or other means) or otherwise disposed within the body interior 6021 and the projected content 630 may be projected on the display sheet 640 (instead of being projected directly onto the back wall of the urinal interior 6021). The display sheet 640 may thus allow for the top mounted analysis portals (e.g., the analysis portals 520 and 620) to be used with those urinals whose constitution does not allow for content to be cohesively projected directly onto the urinal body. The content generators 524, sensors 526, and electronics 528 of the analysis portal 620 may otherwise function in accordance with the disclosure above.

Figure 12:
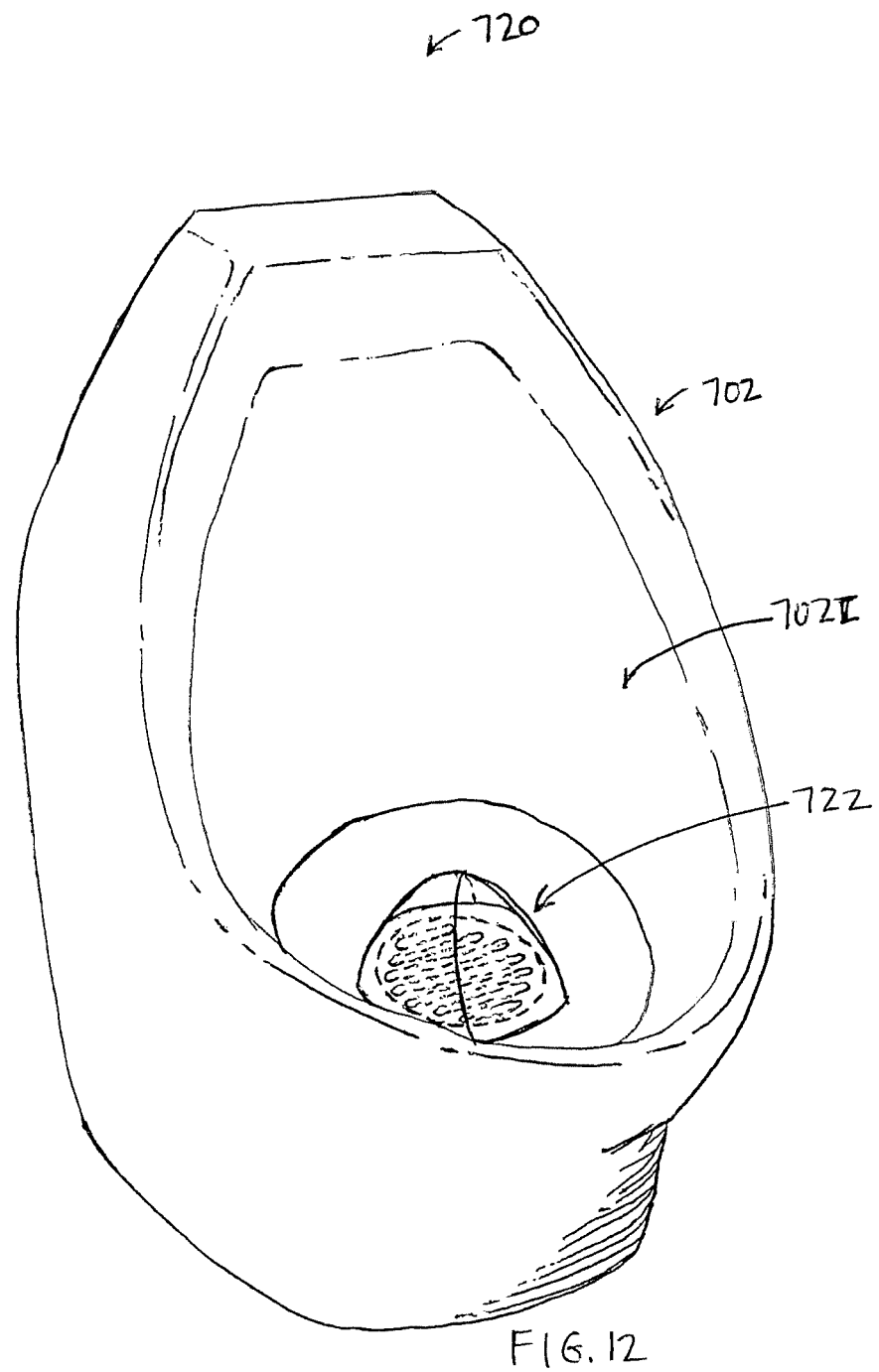
FIG. 12 shows a perspective view of still another embodiment of an analysis portal in use within a urinal.
Figure 13:
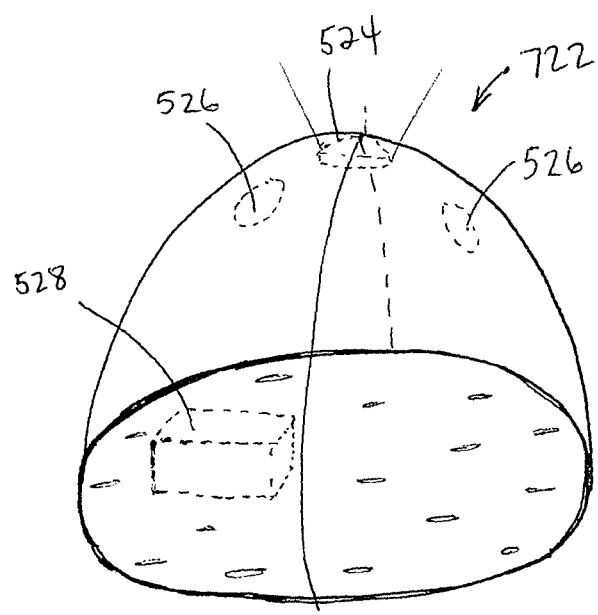
FIG. 13 shows a perspective view of the analysis portal of FIG. 12.

Referring now to FIGS. 12-13, still another alternate embodiment 720 of the analysis portal 520 is illustrated. The analysis portal 720 may be similar to the analysis portal 520 and/or 620, except as specifically noted and/or shown, or as would be inherent. Further, those skilled in the art will appreciate that the analysis portal 520 (and thus the analysis portal 720) may be modified in various ways, such as through incorporating all or part of any of the various described embodiments, for example. For uniformity and brevity, corresponding reference numbers may be used to indicate corresponding parts, though with any noted deviations.

In the urinal 720, the housing 722 is configured as a disk or a dome which may be temporarily (i.e., removably) inserted into the bowl 7021 of the urinal 720. The housing 722 may be molded such that it sits atop and optionally engages with the body 7021 of the urinal 720 (e.g., at the drain) of the urinal 720 in order to prevent undesirable movement of the housing 722. The housing 722, like the housing 622, may include one or more projectors 524, sensors 526, and corresponding electronics 528. The various components 524, 526, and/or 528 may be mounted at desirable locations at or near the surface of the housing 722. As noted below, apertures may be formed into the housing 722 where the projector(s) 524, sensor(s) 526, and electronics 528 are mounted.

In embodiments, the housing 722 may be manufactured from a silicone or similar material, although other materials may additionally or alternately be appropriate. In some embodiments, it may be desirable for the housing 722 material to be substantially transparent such that sensors 526 (e.g., infrared sensors, gesture sensors, etc.) may transmit and receive information through the transparent surface. Here, the housing 722 may be impermeable (i.e., waterproof) such that the components 524, 526, and 528 are not subjected to the urine and water in the urinal 720. Here, urine and/or water may flow down the sides of the housing 722 to the drainage area and through the drain. Therefore, it may be desirable for the bottom of the housing 722 to be slightly elevated above the drainage area (e.g., as a result of being rounded, uneven, etc.) such that the urine and/or water can reach the drain.

In other embodiments, the housing 722 material may be porous or have holes formed therein such that urine from a user may be received into the middle of the housing 722 to. Here, the components 524, 526, and 528 may be individually or collectively encapsulated in a waterproof shelter in order to protect the components from urine and/or water. In embodiments where the housing 722 is porous, the pores may allow urine and/or water to penetrate the housing 722, and flow through the housing 722 to the drain.

As noted above, the projector 524, via the electronics 528, may simply provide lighting to the inner portion of the urinal 7021, as it may be difficult to maintain the correct positioning of the housing 722. However, the projector 524 may be configured to project images into the inner portion of the urinal 7021 as described above. Speakers may additionally be incorporated into the housing 722, which may allow sounds, such as music, special announcements, etc. to be directly relayed to the user. The housing 722 may be further configured to function as an antimicrobial sanitation air freshener. In embodiments, the projector 524, sensors 526, and electronics 528 may be temporarily and removably secured inside a housing 722. For example, the various components 524, 526, and 528 may snap (or otherwise temporarily fasten) into predetermined positions inside the housing 722. When the air-freshening capability of a first housing 722 is depleted, the components 524, 526, and 528 may be removed from the first housing 722 and placed in position in a fresh second housing 722. Alternately, the housing 722 may include air-freshening and/or antimicrobial sanitation elements which may be placed in the center of the housing 722. When a first air-freshening element is depleted, it may be replaced by a second air-freshening element, and so forth.

It shall be recognized by those of skill in the art that the various structures and functionalities described herein regarding urinals 520 and 620 may additionally, or alternately, be incorporated into the urinal 720. Further it shall be understood that the housing 722 may be incorporated into any urinal whether now in use or designed and used at a later date.

Thus, as has been described, an analysis portal (e.g., the analysis portal 120, the analysis portal 520, the analysis portal 620, and/or the analysis portal 720) may be associated with a urinal to impart thereto a novelty factor, allow a user to monitor his health and well-being, communicate generic and/or individualized messages to the user, or to otherwise enhance the experience of a captive user using a urinal. The artisan will appreciate that many different arrangements of the various components depicted, as well as components not shown, are possible without departing from the spirit and scope of the present invention. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out, and need not be carried out in the specific order described.

The invention claimed is:

1. An accessory configured for use with a urinal, said urinal having a body comprising an interior part including a back wall having an opening extending therethrough and a urine monitoring sensor situated within the opening, and an exterior part; said interior part configured to receive urine voided by a user, said accessory comprising:
    a processor;
    a data storage;
    at least one sensor;
    a networking device;
    a projector projecting content onto said interior part; and
    an accessory housing containing said processor, said networking device, and said projector;
    wherein:
    said urine monitoring sensor comprises a sensing part housing and an investigating part housing; said investigating part housing comprising a computing device in data communication with said networking device of the accessory;
    said urine monitoring sensor is situated with said opening in said back wall such that: (a) said sensing part housing is in front of said back wall to allow an upper surface of said sensing part housing to directly receive urine voided by said user; and
    (b) said investigating part housing is rearwardly adjacent said back wall;
    said accessory is disposed atop the exterior part of the urinal such that the projector projects said content for consumption by said user onto said interior part; and
    said projected content includes at least one of general advertising content, personalized content, and a target indicia; said personalized content being projected onto said interior part in response to a wireless communication between said networking device and the urine monitoring sensor and a mobile device of said user.

2. The accessory of claim 1, wherein:
    said projected content includes the target indicia; and
    said target indicia includes a bull's eye said accessory housing is removably coupled to said urinal body.

3. The accessory of claim 2, wherein said accessory housing is portable.

4. The accessory of claim 1 wherein:
    said accessory housing includes a bottom wall removably adhered to a top wall of said exterior part; and
    at least a part of said projector is situated within an aperture defined within said bottom wall.

5. The accessory of claim 1, wherein said at least one sensor comprises a gesture sensor, and wherein said gesture sensor is usable by said user to order an item offered at an entity while said user is at the urinal, the urinal being located within said entity.

6. The accessory of claim 5, further comprising a recommendation generator configured to communicate a recommendation, wherein said recommendation is based off of information received from said urine monitoring sensor in communication with said networking device of said accessory.

7. The accessory of claim 6, further comprising a rewards appraiser configured to award said user a reward based on a reading of said urine monitoring sensor in communication with said networking device of said accessory.

8. The accessory of claim 7, wherein said reward is communicated to said user via said mobile device and is redeemable using said mobile device.

9. The accessory of claim 7, wherein said reward is associated with said entity within which said urinal is located.

10. A method for retrofitting a urinal, said urinal comprising an interior part and an exterior part; said interior part being configured to receive urine voided by a user, said method comprising:
    providing a urinal retrofitting device, comprising:
        a processor;
        a memory for storing historical user information;
        an alert generator;
        a projecting device;
        a sensor;
        a networking device; and a device housing for housing said processor, said sensor, said networking device, and said projecting device;

locating said projecting device in said device housing such that said projecting device projects content on said interior part;

forming an opening through said interior part of said urinal;

providing a urine monitoring sensor comprising a sensing part housing and an investigating part housing; said investigating part housing comprising a computing device in data communication with said networking device of the accessory;

situating said urine monitoring sensor within said opening in said interior part, such that:

(a) said sensing part housing extends into said interior part to allow an upper surface of said sensing part housing to directly receive urine voided by said user; and (b) said investigating part housing is rearwardly adjacent a back wall defining said interior part;

wherein:
user information is transmitted from said urine monitoring sensor to said urinal retrofitting device via said networking device upon said user voiding urine onto said upper surface of said sensing part housing; and
an alert is generated by the alert generator when said urinal retrofitting device receives said information from said urine monitoring sensor.

11. The method of claim 10, wherein said alert is configured as content for said projecting device, said content being projected on said interior part.

12. The method of claim 10, wherein:
said projecting device projects a target indicia;
said projecting device is configured to produce a visible change in said target indicia;
said target indicia includes a bowling pin;
said visible change includes a movement in said bowling pin.

13. The method of claim 10, further comprising a step of projecting on said interior part individualized content tailored to preferences made by said user.

14. The method of claim 13, further comprising a step of projecting said individualized content in response to a wireless communication between said accessory and a mobile device of said user.

15. An accessory configured for use with a urinal, said urinal having a body comprising an interior part including a back wall having an opening extending therethrough and a urine monitoring sensor situated within the opening, and an exterior part; said interior part configured to receive urine voided by a user, said accessory comprising:

a processor;
a sensor;
a networking device; and
a display device for displaying content inside said interior part; and wherein:
said urine monitoring sensor comprises a sensing part housing and an investigating part housing; said investigating part housing comprising a computing device in data communication with the networking device of said accessory;
said urine monitoring sensor is situated within said opening in said back wall such that: (a) said sensing part housing is in front of said back wall to allow an upper surface of said sensing part housing to directly receive urine voided by said user; and (b) said investigating part housing is rearwardly adjacent said back wall;
said urine monitoring sensor senses at least one characteristic of urine voided by said user on said interior part, said characteristic being transmitted to said accessory via said computing device; and
said user is apprised of said characteristic in real time via said display device.

16. The accessory of claim 15, further comprising a global positioning system to determine a location of said accessory.

17. The accessory of claim 15, wherein said display device is a projector.

18. The accessory of claim 15, wherein said urinal comprises stainless steel.

19. The accessory of claim 17, wherein said sensor is a gesture sensor, and wherein said displayed content is alterable by said user using a gesture.

20. The accessory of claim 15 further comprising an alert generator for generating an alert based on a determination of a health condition by said urine monitoring sensor.

* * * * *